United States Patent
Azuma et al.

(10) Patent No.: US 10,995,319 B2
(45) Date of Patent: May 4, 2021

(54) METHOD FOR PRODUCING SHEET-LIKE PANCREATIC ISLET

(75) Inventors: Koji Azuma, Naruto (JP); Yasutaka Fujita, Naruto (JP); Hiroshi Yaguchi, Naruto (JP); Miwa Harada, Naruto (JP)

(73) Assignee: OTSUKA PHARMACEUTICAL FACTORY, INC., Naruto (JP)

( * ) Notice: Subject to any disclaimer, the term of this patent is extended or adjusted under 35 U.S.C. 154(b) by 29 days.

(21) Appl. No.: 14/110,638

(22) PCT Filed: Apr. 6, 2012

(86) PCT No.: PCT/JP2012/059441
§ 371 (c)(1),
(2), (4) Date: Nov. 19, 2013

(87) PCT Pub. No.: WO2012/137896
PCT Pub. Date: Oct. 11, 2012

(65) Prior Publication Data
US 2014/0073051 A1    Mar. 13, 2014

(30) Foreign Application Priority Data
Apr. 8, 2011   (JP) .............................. JP2011-086336

(51) Int. Cl.
*C12N 5/071*   (2010.01)
*C07K 14/705*  (2006.01)

(52) U.S. Cl.
CPC .......... *C12N 5/0676* (2013.01); *C07K 14/705* (2013.01); *C07K 2319/30* (2013.01); *C12N 2500/02* (2013.01); *C12N 2533/50* (2013.01)

(58) Field of Classification Search
None
See application file for complete search history.

(56) References Cited

U.S. PATENT DOCUMENTS

| | | |
|---|---|---|
| 2007/0072292 A1 | 3/2007 | Tsang et al. |
| 2007/0155013 A1 | 7/2007 | Akaike et al. |
| 2008/0103606 A1 | 5/2008 | Berkland et al. |
| 2008/0274950 A1* | 11/2008 | Kilshaw et al. ................... 514/8 |
| 2012/0210451 A1 | 8/2012 | Shimizu et al. |

FOREIGN PATENT DOCUMENTS

| WO | WO 2005/090557 A1 | 9/2005 |
|---|---|---|
| WO | WO 2011/016423 A1 | 2/2011 |

OTHER PUBLICATIONS

Haque et al., "Artificial extracellular matrix for embryonic stem cell cultures: a new frontier of nanobiomaterials", Science and Technology of Advanced Materials, 2010, vol. 11, pp. 1-9.*
Carvell et al., "E-cadherin Interactions Regulate Beta-Cell Proliferation in islet-like Structures", Cell Physiology and Biochemistry, 2007, vol. 20, pp. 617-626.*
Williams et al, "Adhesion of Pancreatic Beta Cells to Biopolymer Films", Biopolymers, 2009, 91(8), pp. 676-685. (Year: 2009).*
Dahl et al., *Development*, 122(9): 2895-2902 (1996).
Hannachi et al., *Biomaterials*, 30(29): 5427-5432 (2009).
Semler et al., *Tissue Engineering*, 11(5/6): 734-750 (2005).
European Patent Office, Extended European Search Report in European Patent Application No. 12767379.6 (dated Oct. 28, 2014).
Dang et al., *Stem Cells*, 22: 275-282 (2004).
Gumbiner, Barry M., *The Journal of Cell Biology*, 148(3): 399-403 (2000).
Haque et al., *Biomaterials*, 32: 2032-2042 (2011).
Larue et al., *Development*, 122: 3185-3194 (1996).
Nagaoka et al., *BMC Developmental Biology*, 10: 60 (2010).
Nagaoka et al., *The Journal of Biological Chemistry*, 283(39): 26468-26476 (2008).
Nagaoka et al., *PLoS One*, 1(1): e15 [doi:10.1371/journal.pone.0000015] (2006).
Nagaoka et al., *Protein Engineering*, 16(4): 243-245 (2003).
Noguchi et al., *Cell Transplantation*, 18: 541-547 (2009).
Parnaud et al., *Endocrinology*, 152(12): 4601-4609 (2011).
Shimizu et al., *Biomaterials*, 30: 5943-5949 (2009).
Takeichi, Masatoshi, *Current Opinion in Cell Biology*, 7: 619-627 (1995).
Yamaoka et al., *International Journal of Molecular Medicine*, 3: 247-261 (1999).
Japanese Patent Office, International Search Report in International Patent Application No. PCT/JP2012/059441 (dated Jul. 10, 2012).
International Bureau of WIPO, International Preliminary Report on Patentability in International Patent Application No. PCT/JP2012/059441 (dated Oct. 8, 2013).
Ezashi et al., "Low $O_2$ tensions and the prevention of differentiation of hES cells," *Proc. Natl. Acad. Sci. U.S.A.*, 102(13): 4783-4788 (2005).
Nagaoka et al., "Design of the Artificial Acellular Feeder Layer for the Efficient Propagation of Mouse Embryonic Stem Cells," *J. Biol. Chem.*, 283(39): 26468-26476 (2008).

* cited by examiner

*Primary Examiner* — Laura Schuberg
(74) *Attorney, Agent, or Firm* — Leydig, Voit & Mayer, Ltd.

(57) ABSTRACT

The present invention provides a method of producing a sheet-like pancreatic islet, comprising culturing an isolated pancreatic islet in a culture vessel, wherein a polypeptide comprising an EC1 domain of E-cadherin and having a binding ability to said E-cadherin is fixed on or applied to a surface of a solid phase, while being adhered to the solid phase surface for a period sufficient for the pancreatic islet to take a sheet-like form.

2 Claims, 4 Drawing Sheets
Specification includes a Sequence Listing.

(A)

(B)

n=3, mean ± S.D., *p<0.05

(mean±SD., n>15, *: p< 0.05)

METHOD FOR PRODUCING SHEET-LIKE PANCREATIC ISLET

CROSS-REFERENCE TO RELATED APPLICATIONS

This patent application is the U.S. national phase of International Patent Application No. PCT/JP2012/059441, filed Apr. 6, 2012, which claims the benefit of Japanese Patent Application No. 2011-086336, filed on Apr. 8, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 45,704 bytes ASCII (Text) file named "714383 Sequence-Listing.txt," created Oct. 7, 2013.

TECHNICAL FIELD

The present invention relates to a production method of a sheet-like pancreatic islet having resistance to low oxygen conditions, a pancreatic islet culture, and a kit for producing a sheet-like pancreatic islet.

BACKGROUND ART

Cell-based therapy utilizing pancreatic islet has been developed as a promising novel approach for treating insulin-dependent diabetes (DM). As compared to the total organ transplantation of pancreas, an islet cell-based treatment is advantageous in that it makes minimum insult and stay in the hospital after treatment can be short. In recent international clinical trials, it has been reported that 44% of DM patients one year after the transplantation of islet cells successfully recovered insulin production, and stably maintained glycemic profile. However, two years after the transplantation, the survival rate of the transplanted islet cells drastically decreased to 14%. It is evident, therefore, that optimization of the conditions for maximizing the life extension of the transplanted cell lineage is necessary for advancing the pancreatic islet-based therapy of DM. Therefore, various culture methods have been studied to increase the function and survival rate of pancreatic islet to be used for transplantation.

In conventional general in vitro culture methods of pancreatic islet, the cells in the pancreatic islet collected from the body are deprived of the oxygen supply system performed in vivo and maintained in the form of a clump, and therefore, they are not supplied with sufficient oxygen and the pancreatic islet function disappears.

To solve the above-mentioned problem, a technique for subcutaneously transplanting an islet cell sheet has been developed (non-patent document 1). In this technique, an isolated pancreatic islet is treated with trypsin-EDTA to disperse the islet cells to a single cell state, the obtained pancreatic islet cells are plated on a plate coated with laminin-5, and the culture temperature is lowered to 20° C. for 20 min after the cell reached confluency, whereby the pancreatic islet cells can be recovered as a uniformly-spread tissue sheet.

In the meantime, E-cadherin (E-cad) is a $Ca^{2+}$-dependent cell-cell adhesion molecule (non-patent documents 2, 3), and is essential for intercellular adhesion and colony formation of mouse embryonic stem cells (ES cell) (non-patent documents 4, 5).

It has been reported that mouse and human ES cells can be successfully maintained on a dish coated with a fusion protein composed of the extracellular domain of E-cadherin and IgG Fc domain (non-patent document 6) (patent documents 1, non-patent documents 7, 8, 9). Although mouse ES cells do not form a colony on a culture dish coated with an E-cad-Fc fusion protein, they maintain pluripotency and can generate a germ line competent chimera mouse (non-patent documents 7, 8). In these general culture methods of ES cells, when single-celled ES cells are added, cell-to-cell adhesion occurs on a culture dish to form a clump. However, on a culture dish coated with an E-cad-Fc fusion protein, the single-celled ES cells can be cultured as they are. In addition, differentiation of mouse ES cells to liver cells on a culture dish coated with a mouse E-cad-Fc fusion protein has been reported (non-patent document 10).

DOCUMENT LIST

Patent Document patent document 1: WO2005/090557

Non-Patent Documents non-patent document 1: Biomaterials, vol. 30, pp. 5943-5949, 2009
non-patent document 2: Curr Opin Cell Biol, vol. 7, pp. 619-627, 1995
non-patent document 3: The Journal of Cell Biology, vol. 148, p. 399-404, 2000
non-patent document 4: Development, vol. 122, pp. 3185-3194, 1996
non-patent document 5: Stem Cells, vol. 22, pp. 275-282, 2004
non-patent document 6: Protein Engineering, vol. 16, no. 4, pp. 243-245, 2003
non-patent document 7: PLoS ONE, issue 1, e15, 2006
non-patent document 8: The Journal of Biological Chemistry, vol. 283, no. 39, pp. 26468-26476, 2008
non-patent document 9: BMC Developmental Biology, vol. 10, 60, 2010
non-patent document 10: Biomaterials, vol. 32, no. 8, pp. 2032-2042, 2011
non-patent document 11: Cell Transplant., vol. 18, no. 5, pp. 541-547, 2009

SUMMARY OF THE INVENTION

Problems to be Solved by the Invention

Conventionally, when a sheet-like pancreatic islet is prepared by planarizing the pancreatic islet, an enzyme treatment of pancreatic islet with trypsin-EDTA to give single cells is essential to meet the physical requirements. However, pancreatic islet has been reported to have a problem that glucose responsiveness remarkably decreases due to the influence of trypsin (non-patent document 11), and the sugar responsiveness of the sheet-like pancreatic islet obtained by this method is considered to decrease.

The present invention aims to resolve the problem of decrease of glucose responsiveness, and provide a method of producing a sheet-like pancreatic islet having resistance to low oxygen conditions.

Means of Solving the Problems

In an attempt to solve the above-mentioned problem, the present inventors first cultured pancreatic islet directly as a clump on a non-treated plate, without a trypsin treatment. However, the pancreatic islet was still in the form of a clump and did not take a sheet-like structure. In addition, this culture method was considered to easily induce cell death under low oxygen conditions, since it lacks the oxygen supply system to the cells in pancreatic islet, which is present in vivo. Therefore, a sheet-like structure having resistance to low oxygen conditions is preferable. However, when a sheet-like pancreatic islet is prepared using a general trypsin-EDTA treatment to form single cells, the glucose responsive function is considered to markedly decrease, since the cell-cell adhesion that controls the glucose responsive function is lost. Therefore, they intensively studied the culture conditions and found that the pancreatic islet shows a sheet-like structure by culturing the pancreatic islet on a culture dish wherein a polypeptide comprising an EC1 domain of E-cadherin and having a binding ability to said E-cadherin is fixed on or applied to a surface of a solid phase, even without dispersing the pancreatic islet to single cells by a trypsin treatment, that a pancreatic islet in a sheet-like tissue form shows higher glucose responsiveness than a pancreatic islet forming a clump and has resistance to low oxygen conditions. Further studies have resulted in the completion of the present invention.

Accordingly, the present invention relates to the following.

[1] A method of producing a sheet-like pancreatic islet, comprising culturing an isolated pancreatic islet in a culture vessel, wherein a polypeptide comprising an EC1 domain of E-cadherin and having a binding ability to said E-cadherin is fixed on or applied to a surface of a solid phase, while being adhered to the solid phase surface for a period sufficient for the pancreatic islet to take a sheet-like form.

[2] The production method of [1], wherein the polypeptide comprises an extracellular domain of E-cadherin.

[3] The production method of [1], wherein the polypeptide is a fusion polypeptide comprising an extracellular domain of E-cadherin and an Fc region of immunoglobulin.

[4] A pancreatic islet culture, comprising a culture vessel, wherein a polypeptide comprising an EC1 domain of E-cadherin and having a binding ability to said E-cadherin is fixed on or applied to a surface of a solid phase, and a sheet-like pancreatic islet that can be cultured in a state wherein the sheet-like pancreatic islet adheres to the polypeptide.

[5] A kit for producing a sheet-like pancreatic islet, comprising a culture vessel, wherein a polypeptide comprising an EC1 domain of E-cadherin and having a binding ability to said E-cadherin is fixed on or applied to a surface of a solid phase, and an isolated pancreatic islet.

Effect of the Invention

Using the method of the present invention, a sheet-like pancreatic islet having resistance to low oxygen conditions can be produced without performing a trypsin treatment while suppressing a decrease in the glucose responsive function compared to conventional culture methods.

In general, the pancreatic islet does not show oxygen shortage since blood vessel induction into the pancreatic islet tissue occurs in the body. However, in the case of a transplanted pancreatic islet, the cell death of the pancreatic islet may be induced by oxygen shortage under the environment of low oxygen conditions at the transplantation site. Using the sheet-like pancreatic islet obtained by the method of the present invention, oxygen can be efficiently supplied to each cell even in a low oxygen state, and the cell death of the pancreatic islet is suppressed even under low oxygen conditions. Moreover, since a sheet-like form of pancreatic islet is considered to increase the glucose responsive function, it is advantageous for the transplantation therapy.

DESCRIPTION OF EMBODIMENTS

Figure 1:
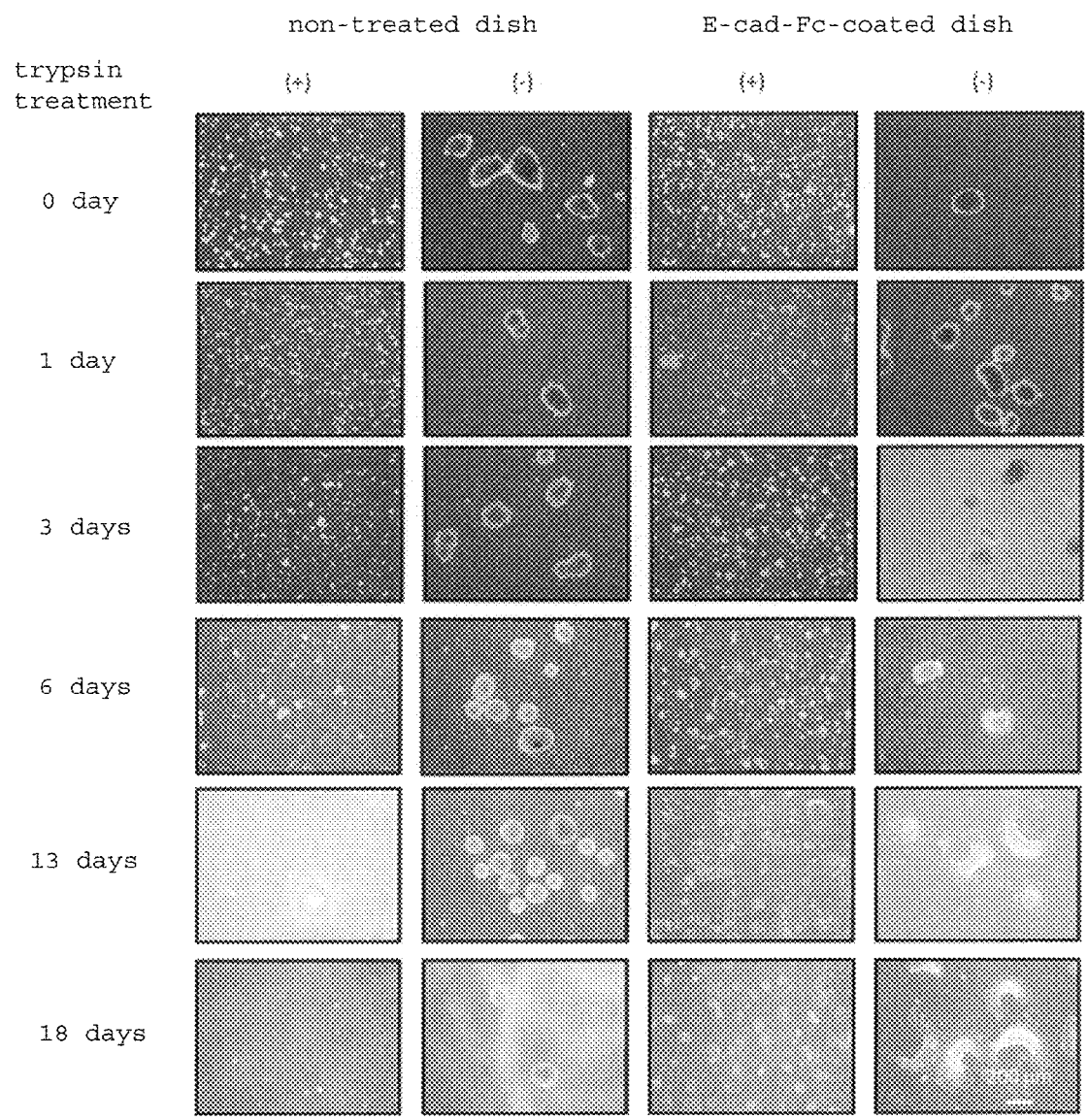
FIG. 1 shows the morphology of pancreatic islet cultured on an E-cad-Fc-coated dish and a non-treated dish at respective culture days with or without a trypsin treatment.

The present invention provides a method of producing a sheet-like pancreatic islet, comprising culturing an isolated pancreatic islet in a culture vessel, wherein a polypeptide comprising an EC1 domain of E-cadherin and having a binding ability to said E-cadherin is fixed on or applied to a surface of a solid phase, while being adhered to the solid phase surface for a period sufficient for the pancreatic islet to take a sheet-like form.

Pancreatic islet is a cell clump interspersed in the parenchyma of pancreas, which contains a cell (A cell) that secretes glucagon, β cell (B cell) that secretes insulin and δ cell (D cell) that secretes somatostatin.

The pancreatic islet to be used in the present invention is isolated from a mammal. Examples of the mammal include, but are not limited to, laboratory animals such as rodents such as mice, rats, hamsters and guinea pigs, and rabbits; domestic animals such as pigs, bovines, goat, horses, sheep and minks; companion animals such as dogs and cats; primates such as humans, monkeys, cynomolgus monkey, rhesuses, marmosets, orangutans and chimpanzees; and the like. The mammal is preferably rodents (mouse etc.) or primates (human etc.).

A pancreatic islet can be isolated from a mammalian pancreas by a method known per se using collagenase digestion. For example, it can be isolated by static collagenase digestion and subsequent centrifugation in Ficoll-Conray gradient (Sutton, R., 1986, Transplantation, 42:689-691/ Ohtsuka, K., et. al., 1997, Transplantation, 64: 633-639).

When the pancreatic islet is dispersed to a single cell state by a treatment with a protease such as trypsin and the like, the resulting sheet-like pancreatic islet may have reduced glucose responsiveness. In the production method of the present invention, therefore, pancreatic islet in a cell clump state is cultured in a culture vessel, wherein a polypeptide comprising an EC1 domain of E-cadherin and having a binding ability to said E-cadherin is fixed on or applied to a surface of a solid phase, without being dispersed to a single cell state by protease. The cell clump means a state wherein plural cells form one clump by mutually adhering and the like. Depending on the mammalian species, about 10-10000 islet cells are generally contained in one pancreatic islet. Therefore, the number of islet cells contained in a pancreatic islet (cell clump) subjected to the above-mentioned culture is also generally within the range of 10-10000.

In the present invention, an isolated pancreatic islet is cultured in a culture vessel, wherein a polypeptide comprising an EC1 domain of E-cadherin and having a binding ability to said E-cadherin is fixed on or applied to a surface of a solid phase. As a result, E-cadherin expressed on a surface of the cells constituting the pancreatic islet binds to the polypeptide, which in turn results in the adhesion of the pancreatic islet to the surface of the solid phase.

E-cadherin is a known adhesion molecule involved in a $Ca^{2+}$-dependent intercellular adhesion•binding called adhesion binding or adherens junction. E-cadherin is widely expressed in parenchymal cells of internal organs such as liver, kidney, lung and the like, epithelial cells such as keratinocyte and the like, and known to be an important adhesion molecule responsible for intercellular adhesion thereof (Mareel et al., Int. J. Dev. Biol. 37: 227, 1993; Mays et al., Cord Spring Harb. Symp. Quant. Biol. 60: 763, 1995; El-Bahrawy & Pignatelli, Microsc. Res. Tech. 43:224, 1998; Nollet et al., Mol. Cell. Biol. Res. Commun. 2: 77, 1999).

E-cadherin to be used in the method of the present invention is generally derived from a mammal. Examples of the mammal include, but are not limited to, laboratory animals such as rodents such as mice, rats, hamsters and guinea pigs, and rabbits; domestic animals such as pigs, bovines, goat, horses, sheep and minks; companion animals such as dogs and cats; primates such as humans, monkeys, cynomolgus monkey, rhesuses, marmosets, orangutans and chimpanzees; and the like. The mammal is preferably rodents (mouse etc.) or primates (human etc.).

with respect to each polypeptide or polynucleotide to be used in the present invention, "derived from organism X" means that the amino acid sequence or nucleic acid sequence of the polypeptide or polynucleotide has the same or substantially the same amino acid sequence or nucleic acid sequence as the amino acid sequence or nucleic acid sequence of the polypeptide or polynucleotide naturally expressed in organism X. The "substantially the same" means that the amino acid sequence or nucleic acid sequence taken note of has not less than 70% (preferably not less than 80%, more preferably not less than 90%, still more preferably not less than 95%, most preferably not less than 99%) identity with the amino acid sequence or nucleic acid sequence of a factor naturally expressed in organism X, and that the function of the factor is retained.

As E-cadherin to be used in the present invention, a pancreatic islet derived from an animal of the same species as the pancreatic islet to be the culture target is preferable. For example, when the present invention is practiced using a pancreatic islet isolated from a mouse, E-cadherin of the mouse is desirably used. In addition, when the present invention is practiced using a pancreatic islet isolated from human, E-cadherin of the human is desirably used. However, an E-cadherin derived from a heterogeneous animal can also be used as long as a sheet-like pancreatic islet can be produced by the production method of the present invention.

Amino acid sequences and cDNA sequences of many E-cadherins derived from mammals are known. Representative cDNA sequence and amino acid of human E-cadherin are shown in SEQ ID NOs: 1 and 2, respectively, and representative cDNA sequence and amino acid of mouse E-cadherin are shown in SEQ ID NOs: 3 and 4, respectively.

E-cadherin is known to homophilically bind via an extracellular region (i.e., with the same molecules). The extracellular region of E-cadherin contains 5 repeat structures consisting of about 110 amino acid residues, which are regions so-called Extracellular Cadherin (EC) domains. For example, in the case of human E-cadherin (SEQ ID NO: 2), each domain of EC1, EC2, EC3, EC4, EC5 corresponds to 157-262, 265-375, 378-486, 487-595, 596-700, respectively (number shows the number of residues in the amino acid sequence of SEQ ID NO: 2). In the case of mouse E-cadherin (SEQ ID NO: 4), each domain of EC1, EC2, EC3, EC4, EC5 corresponds to 159-264, 267-377, 380-488, 489-597, 598-702, respectively (number shows the number of residues in the amino acid sequence of SEQ ID NO: 4).

In general, since the domain (EC1) positioned at the most N-terminal side of cadherin molecule defines the binding specificity of the molecule, i.e., homophilic binding (Nose et al., Cell 61: 147, 1990), the polypeptide to be used in the present invention contains at least the EC1 domain of E-cadherin, and has a binding ability to E-cadherin. In a preferable embodiment, the polypeptide to be used in the present invention contains, in addition to the EC1 domain, one, preferably 2, more preferably 3, still more preferably 4, domains selected from EC2-5. In a more preferable embodiment, the polypeptide to be used in the present invention contains an extracellular region of E-cadherin. In the case of human E-cadherin, the extracellular region corresponds to the 1st-697th amino acids of the amino acid sequence shown by SEQ ID NO: 2. In the case of mouse E-cadherin, the extracellular region corresponds to the 1st-699th amino acids of the amino acid sequence shown by SEQ ID NO: 4.

The polypeptide to be used in the present invention may be a fusion polypeptide containing a sequence derived from E-cadherin and a sequence derived from other protein or peptide. For example, a polypeptide can be purified easily and efficiently by preparing the polypeptide as a fusion polypeptide with Fc region of immunoglobulin or GST (Glutathione-S-Transferase) protein, MBP (Mannose-Binding Protein) protein, avidin protein, H is (oligo•histidine) tag, HA (HemAgglutinin) tag, Myc tag, VSV-G (Vesicular Stromatitis Virus Glycoprotein) tag and the like, and using protein A/G column, specific antibody column and the like. Particularly, Fc fusion polypeptide is preferable for practicing the present invention since an ability to adsorb to a culture material using polystyrene and the like is enhanced.

Many genes encoding the Fc regions of immunoglobulin have already been isolated and identified in mammals including human. There are also many reports on the base sequences thereof and, for example, the sequence information of the base sequences of Fc regions of human IgG1, IgG2, IgG3, and IgG4 is available from public DNA databases such as NCBI and the like, and registered as accession numbers: AJ294730, AJ294731, AJ294732 and AJ294733, respectively. Therefore, those of ordinary skill in the art can obtain and use a cDNA encoding an Fc region by designing a primer or probe specific to an Fc region and using a general molecular biological method. In this case, while the animal species and subtype of a gene encoding an Fc region to be used are not particularly limited, a gene encoding an Fc region of human IgG1 or IgG2, mouse IgG2a or IgG2b and the like showing strong affinity for protein A/G is preferable. In addition, a method of enhancing the affinity for protein A by introducing a mutation into the Fc region is also known (Nagaoka et al., Protein Eng. 16: 243, 2003), and an Fc protein added with a genetic modification by this method can also be used.

Examples of the polypeptide preferably used in the present invention include polypeptide containing an extracellular region of E-cadherin disclosed in Nagaoka et al., Biotechnol. Lett. 24: 1857, 2002 and Protein Eng. 16: 243, 2003.

In addition, purified recombinant proteins (Recombinant Human/Mouse E-cadherin-Fc Chimera; R&D systems, Genzyme Techne) prepared by introducing a fusion gene wherein a sequence encoding an Fc region of human IgG and a cDNA of His-tag sequence are linked to a cDNA encoding a mouse or human extracellular region of E-cadherin into mouse cells and expressing same are commercially available, and these can also be applied to the present invention. Moreover, a culture dish having the bottom coated with E-cadherin-Fc is commercially available from SUMITOMO BAKELITE CO., LTD. and the like, and this can also be applied to the present invention.

The above-mentioned polypeptide is preferably isolated or purified. Being "isolated or purified" means being artificially placed in a state different from that naturally present, for example, an operation to remove components other than the object component from the naturally-present state has been applied. The purity of the isolated or purified the above-mentioned polypeptide (proportion of the above-mentioned polypeptide weight to the total polypeptide weight) is generally not less than 30%, preferably not less than 50%, more preferably not less than 70%, still more preferably not less than 90% (e.g., 100%).

The above-mentioned polypeptide can be produced by culturing mammalian cells such as COS cell, 293 cell, CHO cell and the like introduced with an expression vector capable of expressing the polypeptide, and isolating and purifying the polypeptide from the culture by a biochemical method known per se. In the expression vector, a nucleic acid (DNA etc.) encoding the polypeptide is linked to a nucleic acid sequence enabling the transcription and expression of genes in a wide range of mammalian cells, what is called a promoter sequence, in a manner enabling transcription and expression under the regulation of the promoter. The gene to be transcribed and expressed is desirably linked with polyA addition signal. Preferable promoter includes promoters derived from virus such as SV (Simian Virus) 40 virus, cytomegalovirus (CMV), Rous sarcoma virus and the like, β-actin promoter, EF (Elongation Factor) 1α promoter and the like.

The material for constituting a solid phase in a culture vessel is not particularly limited as long as it can achieve production of a sheet-like pancreatic islet when used for the production method of the present invention, a material having no cytotoxicity, permitting sterilization and having affinity for protein can be generally used. In general, plastic or glass materials are preferable. The material may be a metal or ceramic, and is not limited to a certain material.

The plastic material is a thermosetting or thermoplastic polymer superior in moldability and, for example, polystyrene, methacrylic resin, polymethylpentene, ethylene-vinyl-alcohol copolymer, polypropylene, cellulose, polyethylene, polysulfone, polyacrylonitrile and the like can be used without limitation thereto.

The glass material means one resulting from vitrification of silicate, borate, phosphate and the like without crystallization. Since vitrification tendency is strong, silicate glass is preferable. In addition, crystallized glass which is one kind of a composite material produced by heat-treating silicate glass is more preferable since it has rich moldability and high impact resistance.

Examples of the culture vessel include, but are not limited to, petri dish, plate, flask, bottle and the like. The form of the culture vessel is not particularly limited as long as the pancreatic islet adheres to a solid phase surface and can achieve production of a sheet-like pancreatic islet when applied to the method of the present invention.

The solid phase surface refers to a part enabling adhesion of a pancreatic islet to be cultured to a solid phase, when the pancreatic islet is cultured while being adhered to the solid phase in a culture vessel, for example, a part to be in contact with a medium when the medium is added.

As a method for fixing or coating a polypeptide onto a solid phase surface, a method using a non-covalent bond (hydrogen bond, ionic bond, hydrophobic bond etc.), a covalent bond and the like can be generally used.

Examples of the method for fixing or coating a polypeptide onto a solid phase surface by using a non-covalent bond include a method of standing still the solid phase surface in a suitable buffer (e.g., phosphate buffer etc.) containing the polypeptide. The conditions (buffer type, concentration of polypeptide in buffer, standing time etc.) of the method can be appropriately determined as long as it can achieve production of a sheet-like pancreatic islet when used for the production method of the present invention. For example, when a polypeptide is a fusion polypeptide containing an extracellular region of mouse or human E-cadherin and an Fc region of mouse or human IgG, and the material constituting the solid phase is a plastic (e.g., polystyrene), the polypeptide is fixed or applied onto the surface of the solid phase by standing the solid phase for about 0.5-24 hr in a neutral phosphate-buffered saline containing a polypeptide at a concentration of generally 0.01-1000 µg/mL (preferably 0.1-200 µg/mL, more preferably 1-50 µg/mL).

Examples of the method for fixing or coating a polypeptide by using a covalent bond include a method of introducing a functional group into a solid phase surface by treating the solid phase surface with a silane coupling agent having a functional group, and binding the polypeptide to the functional group with a crosslinking agent (see, for example, JP-A-2003-189843). Examples of the functional group that can be introduced include amino group, aldehyde group, epoxy group, carboxyl group, hydroxyl group, thiol group and the like. Examples of the silane coupling agent include γ-aminopropyltriethoxysilane, N-β-(aminoethyl)γ-aminopropyltrimethoxysilane, N-β-(aminoethyl)γ-aminopropylmethyldimethoxysilane and the like. Examples of the crosslinking agent include diethylene glycol diglycidyl ether, 1-ethyl-3-(3-dimethylaminopropyl)-carbodiimide, N,N'-carbodiimidazole, glutaraldehyde, anhydrous succinic acid, anhydrous phthalic acid, hexamethylenediisocyanate and the like.

In this way, an isolated pancreatic islet is cultured in a culture vessel, wherein a polypeptide comprising an EC1 domain of E-cadherin and having a binding ability to said E-cadherin is fixed on or applied to a surface of a solid phase, whereby E-cadherin expressed on the surface of the cells constituting the pancreatic islet binds to the polypeptide, as a result of which the pancreatic islet adheres to the solid phase surface.

While the strength of the adhesion of the pancreatic islet to the solid phase surface is not particularly limited as long as it can achieve the production of the sheet-like pancreatic islet by the production method of the present invention, it is generally a strength that prevents dissociation unless a physical and/or a chemical treatment are/is applied. Examples of the physical treatment include a treatment by pipetting or tapping and the like. Examples of the chemical treatment include a treatment with a chelating agent such as EDTA, EGTA and the like, a treatment with a protease such as trypsin and the like, and the like.

In the production method of the present invention, as a basal medium of a medium used for culturing a pancreatic islet, one known per se and usable for in vitro culture of pancreatic islet can be used, and is not particularly limited as long as it can achieve the production of the sheet-like pancreatic islet by the production method of the present invention. For example, DMEM, EMEM, RPMI-1640, α-MEM, F-12, F-10, M-199, HAM and the like can be mentioned. In addition, a medium altered for culturing pancreatic islet and the like may be used, and a mixture of the above-mentioned basal media may also be used.

A medium used for culturing pancreatic islet in the production method of the present invention can contain an additive known per se and generally used for the tissue culture of pancreatic islet. While the additive is not particularly limited as long as it can achieve the production of the sheet-like pancreatic islet by the production method of the present invention, for example, growth factors (e.g., insulin etc.), iron sources (e.g., transferrin etc.), polyamines (e.g., putrescine etc.), minerals (e.g., sodium selenate etc.), saccharides (e.g., glucose etc.), organic acids (e.g., pyruvic acid, lactic acid etc.), serum proteins (e.g., albumin etc.), amino acids (e.g., L-glutamine etc.), reducing agents (e.g., 2-mercaptoethanol etc.), vitamins (e.g., ascorbic acid, d-biotin etc.), antibiotics (e.g., streptomycin, penicillin, gentamicin etc.), buffering agents (e.g., HEPES etc.) and the like can be mentioned. The additive is preferably contained in a medium at a concentration within the range known per se.

The medium used for culturing a pancreatic islet in the production method of the present invention may contain serum. While the concentration of the serum is not particularly limited as long as it can achieve the production of the sheet-like pancreatic islet by the production method of the present invention, it is generally within the range of 0.1-30 (v/v) %.

As other culture conditions for a pancreatic islet in the production method of the present invention, culture conditions in common use in pancreatic islet tissue culture technology can be used. For example, culturing temperature is normally in the range of about 30-40° C., and preferably exemplified by about 37° C. $CO_2$ concentration is normally in the range of about 1-10%, and preferably exemplified by about 5%. Humidity is normally in the range of about 70-100%, and preferably exemplified by about 95-100%.

In the production method of the present invention, an isolated pancreatic islet is cultured for a period sufficient for taking a sheet-like form in a culture vessel wherein the above-mentioned polypeptide is fixed on or applied to a surface of the solid phase while being adhered to the solid phase surface. When an isolated pancreatic islet is cultured in a culture vessel wherein the above-mentioned polypeptide is fixed on or applied to a surface of the solid phase, the pancreatic islet adheres to the solid phase surface, and spreads over the solid phase surface in time to take a sheet-like form. The "sheet-like" refers to a shape having a sufficiently large length or width (preferably, both) relative to the thickness of the pancreatic islet. For example, the length or width (preferably, both) of the sheet-like pancreatic islet is generally not less than 3-fold, preferably not less than 10-fold, of the thickness. The "thickness" of the pancreatic islet means the thickness of the thickest portion in the direction perpendicular to the solid phase surface of the culture vessel. The "length" of the pancreatic islet means the maximum length in the direction orthogonal to the thickness direction of the aforementioned pancreatic islet. The "width" of the pancreatic islet means the maximum length among the lengths in the direction orthogonal to both the thickness direction and the length direction of the aforementioned pancreatic islet. In one embodiment, the sheet-like pancreatic islet includes a single layer of pancreatic islet cells. The time necessary for taking a sheet-like form varies depending on the animal species from which pancreatic islet is derived, the above-mentioned polypeptide constitution, and culture conditions, and generalization thereof is difficult. When the pancreatic islet of a mouse is cultured in a culture vessel wherein a polypeptide comprising an extracellular region of mouse E-cadherin and an Fc region of IgG is fixed on or applied to a surface of a solid phase, the pancreatic islet begins to spread in about 3 days after the start of the culture, and it takes a sheet-like form in about 6 days to 10 days. Even when a pancreatic islet of other animal species or a polypeptide with other constitution is used, those of ordinary skill in the art can appropriately determine, by reference to this culture period, a period sufficient for pancreatic islet to take a sheet-like form.

While the upper limit of the culture period is not particularly limited as long as the obtained sheet-like pancreatic islet maintains glucose responsiveness, when the culture period becomes long, insulin secretability may decrease. Therefore, the culture period is generally within 8 weeks, preferably within 4 weeks, more preferably within 1 week.

A sheet-like pancreatic islet obtained by the production method of the present invention shows good glucose responsiveness. The glucose responsiveness means an ability to sense an increase in the glucose concentration and secrete insulin. For example, the insulin concentration of a culture medium after culture of a sheet-like pancreatic islet obtained by the production method of the present invention in DMEM containing 4500 mg/l of glucose at 37° C., 5% $CO_2$ for 1 hr is generally not less than 1.5-fold, preferably not less than 2-fold, more preferably not less than 3-fold, of that in a culture medium after culture in DMEM containing 1000 mg/l of glucose at 37° C., 5% $CO_2$ for 1 hr.

In addition, the present invention provides a pancreatic islet culture containing a culture vessel, wherein a polypeptide comprising an EC1 domain of E-cadherin and having a binding ability to said E-cadherin is fixed on or applied to a surface of a solid phase, and a sheet-like pancreatic islet, which enables culture of the sheet-like pancreatic islet while it is adhered to the solid phase surface.

In one embodiment, in the culture, the sheet-like pancreatic islet survives and functions while being adhered to the solid phase surface.

In one embodiment, in the culture, the sheet-like pancreatic islet survives while being adhered to the solid phase surface. In another embodiment, in the culture, the sheet-like pancreatic islet grows while being adhered to the solid phase surface.

The culture refers to a resulting product obtained by culturing tissues and cells.

The definition and embodiment of each term relating to the culture of the present invention are the same as those described for the above-mentioned production method of the present invention.

The culture of the present invention can contain a medium used for the aforementioned method of the present invention, insulin secreted by the pancreatic islet and the like in addition to the above-mentioned culture vessel, and the sheet-like pancreatic islet.

The pancreatic islet culture of the present invention is useful for the practice of the regenerative medicine utilizing the sheet-like pancreatic islet.

A kit for the production of a sheet-like pancreatic islet containing a culture vessel, wherein a polypeptide comprising an EC1 domain of E-cadherin and having a binding ability to said E-cadherin is fixed on or applied to a surface of a solid phase, and an isolated pancreatic islet is provided. Using the kit of the present invention, a sheet-like pancreatic islet can be produced easily by the above-mentioned production method of the present invention.

The definition and embodiment of each term relating to the kit of the present invention are the same as those described for the above-mentioned production method of the present invention.

The kit of the present invention may further contain a reagent used for the above-mentioned production method of the present invention. Examples of the reagent include proteases such as collagenase and the like used for the isolation of a pancreatic islet, medium, serum and the like.

The contents disclosed in any publication cited in the present specification, including patents and patent applications, are hereby incorporated in their entireties by reference, to the extent that they have been disclosed herein.

The present invention is explained in more detail in the following by referring to Examples shown below, which are not to be construed as limitative.

EXAMPLES

Example 1

Pancreatic Islet Culture

Pancreatic islet was separated from male mice (body weight 20-25 g, 9-10-week-old, C57BL/6J; CHARLES RIVER LABORATORIES JAPAN, INC.) by a digestion method using collagenase from clostridium histdyticum Type V (GIBCO). The pancreatic islet was separated by a density gradient method using Biocoll Separating Solution (Biocheom AG) and picked up by hand using Pipetman. The separated pancreatic islet was cultured (37° C./$CO_2$; 5%) on a 3.5 cm E-cad-Fc-coated dish (SUMITOMO BAKELITE CO., LTD.) and a non-treated dish (IWAKI) in Dulbecco's Modified Eagle's Medium (DMEM; SIGMA) added with 10 (v/v) % FBS (GIBCO), and 1 (v/v) % Anti-Anti (GIBCO) as an antibiotic. The medium was changed 7 days after the pancreatic islet was plated in the culture vessel, and changed every 3 days thereafter.

Example 2

Observation of Pancreatic Islet Morphology

The separated pancreatic islet was plated on a 3.5 cm E-cad-Fc coated dish (SUMITOMO BAKELITE) and a non-treated dish (IWAKI). Furthermore, pancreatic islet to be single-celled was treated with trypsin-EDTA (GIBCO) for 5 min at 37° C., and pancreatic islet cells dispersed in a single-cell state were plated similarly. The pancreatic islet and pancreatic islet cells single-celled by a trypsin-EDTA treatment were cultured (37° C./$CO_2$; 5%) using Dulbecco's Modified Eagle's Medium (DMEM; SIGMA) added with 10% FBS (GIBCO), and 1 (v/v) % Anti-Anti (GIBCO) as an antibiotic. The medium was changed 7 days after the pancreatic islet was plated in the culture vessel, and changed every 3 days thereafter.

Thereafter, the morphology of the pancreatic islet was observed by an inverted phase contrast microscope (Olympus IX-70) every other day. The results are shown in FIG. 1. When the pancreatic islet was plated on an E-cad-Fc-coated dish, the pancreatic islet spread on the dish in 3 days from the start of the culture, and a sheet-like form was observed in 6 days from the start of the culture. On the other hand, when plated on a non-treated dish (IWAKI), the tissue morphology did not change and the pancreatic islet was still in the form of a clump. Even after culture for 18 days, a sheet-like form could not be afforded. When pancreatic islet cells in a single cell state were plated on an E-cad-Fc-coated dish, adhesion of the cell to the dish was observed. On the other hand, when pancreatic islet cells in a single cell state were plated on a non-treated dish (IWAKI), the cells underwent necrosis.

Example 3

Evaluation of Glucose Responsive Function by Stimulation Index

Figure 2:
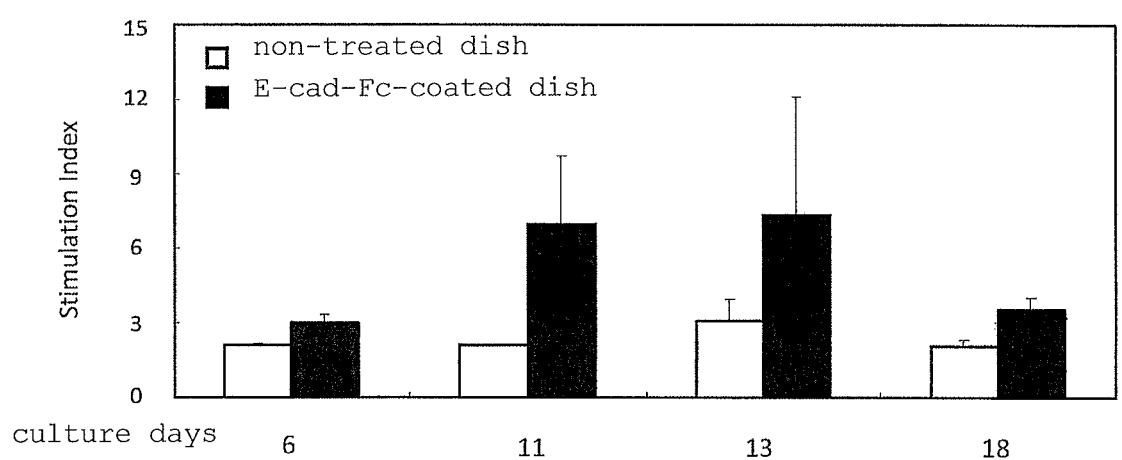
FIG. 2 shows the stimulation index of pancreatic islet on a non-treated dish or an E-cad-Fc-coated dish at respective culture days.

Under the same culture conditions as in Example 1, a pancreatic islet (40 pieces) separated from a mouse was plated and cultured on a 3.5 cm E-cad-Fc-coated dish or a non-treated dish. After the start of the culture, whether the insulin secretion amount of the pancreatic islet can be controlled by the concentration of glucose in the culture medium was examined. The pancreatic islet cultured on the E-cad-Fc-coated dish or non-treated dish was washed twice with a low glucose medium (1,000 mg/l DMEM), thereafter cultured in a low glucose medium (1,000 mg/l DMEM) for 1 hr, and the amount of insulin secreted in the supernatant was taken as an insulin secretion amount with low concentration glucose. Thereafter, the pancreatic islet was washed twice with a high glucose medium (4,500 mg/l DMEM), cultured in a high glucose medium (4,500 mg/l DMEM) for 1 hr, and the amount of insulin secreted in the supernatant was taken as an insulin secretion amount with high concentration glucose. The recovered supernatant was subjected to the measurement of an insulin secretion amount of the pancreatic islet on the non-treated dish and E-cad-Fc-coated dish, by using Levis insulin-mouse (Shibayagi Co. Ltd.), which is an ELISA (Enzyme-Linked ImmunoSorbent Assay) kit. To evaluate the function of the pancreatic islet, Stimulation Index (SI; ratio of insulin secretion amount under high concentration glucose environment to insulin secretion amount under low concentration m glucose environment) was calculated (FIG. 2).

On each culture day, the pancreatic islet showed glucose responsiveness on the non-treated dish and the E-cad-Fc-coated dish, whereby an insulin secretion ability was confirmed. As a result of the calculation of the Stimulation index, the pancreatic islet cultured on the E-cad-Fc-coated culture vessel showed a pancreatic islet function equal to or not less than that of the pancreatic islet cultured on the non-treated dish (FIG. 2).

Example 4

Influence of Trypsin Treatment on Glucose Responsive Function

A mouse-derived pancreatic islet (40 pieces) was plated on a 3.5 cm E-cad-Fc-coated dish or a non-treated dish. Furthermore, a mouse-derived pancreatic islet was incubated in trypsin-EDTA (GIBCO) at 37° C., 5 min to prepare pancreatic islet cells in a single-cell state, which were plated in the same manner as with pancreatic islet. At 11 days from the start of the culture, the glucose responsive function of the pancreatic islet and pancreatic islet cells was examined by SI. The evaluation by ELISA was performed by the same method as in Example 3. In addition, SI on each culture day was calculated.

Figure 3:
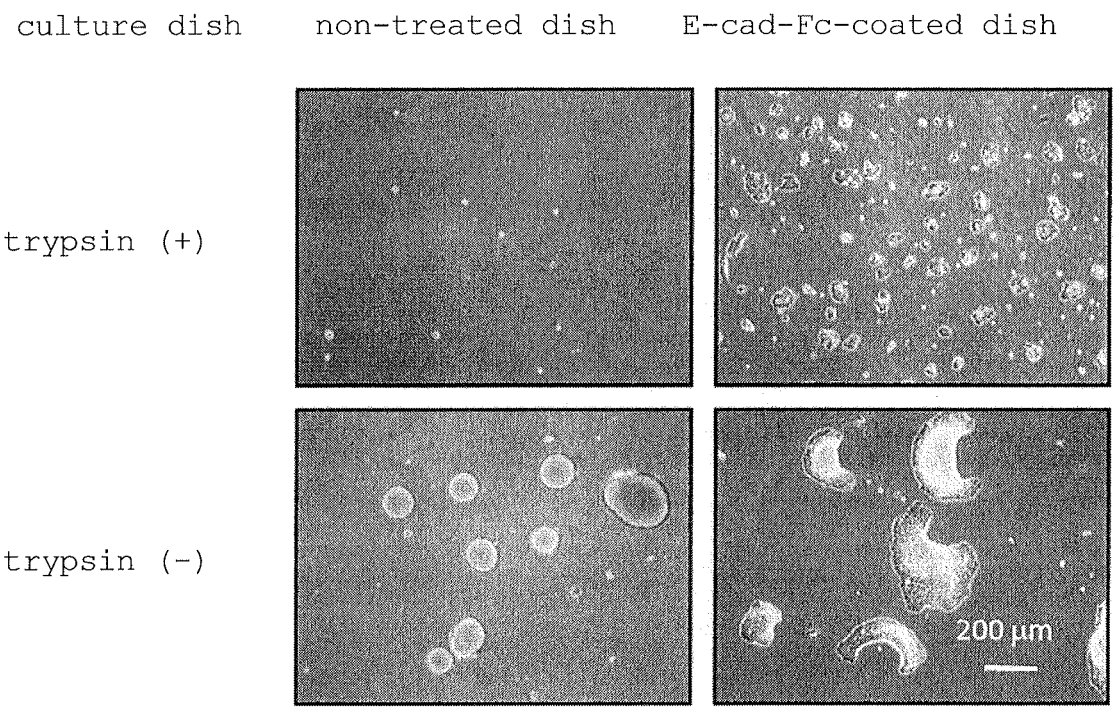
FIG. 3 shows (A) cell morphology of pancreatic islet and (B) Stimulation Index (n=3, mean±S.D., *p<0.05) under respective culture conditions 11 days after the culture.
Figure 3:
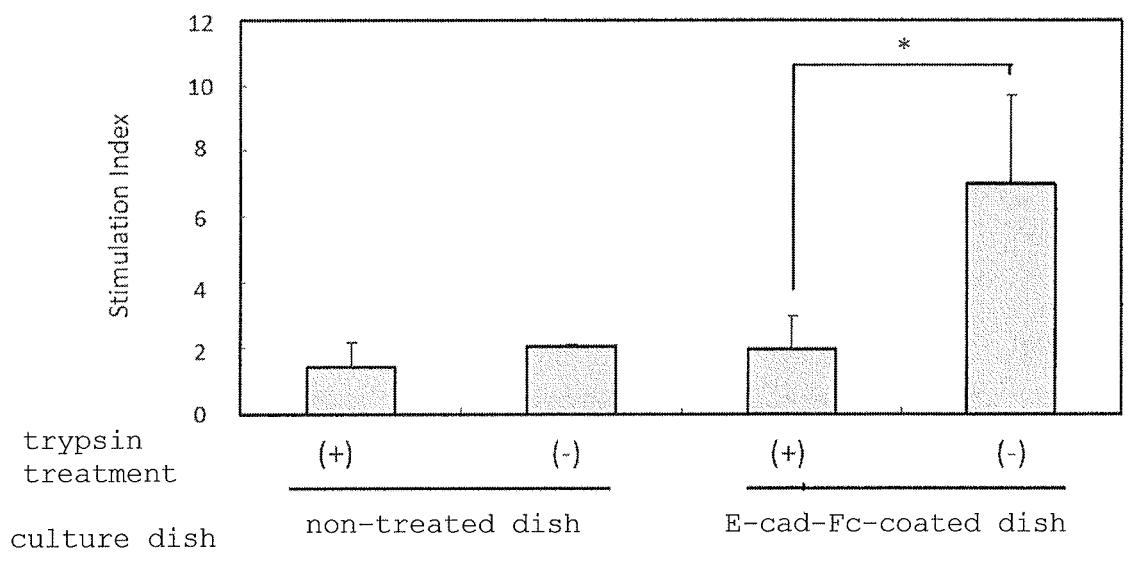

The insulin secretion amount of the pancreatic islet cells dispersed by a trypsin-EDTA treatment decreased on both the non-treated dish and E-cad-Fc coated dish, as compared to that of a pancreatic islet without the treatment. In addition, the stimulation index of the pancreatic islet cells dispersed by a trypsin-EDTA treatment on an E-cad-Fc-coated dish also decreased as compared to that of a pancreatic islet without the treatment (FIG. 3). Therefore, it was suggested that a trypsin-EDTA treatment decreases the glucose responsive function.

Example 5

Measurement of Cell Death Induction Rate in Pancreatic Islet Under Low Oxygen Conditions Under the same culture conditions as in Example 1, a pancreatic islet separated from a mouse was plated and cultured for 1 week on a 3.5 cm E-cad-Fc-coated dish or a non-treated dish. The pancreatic islet on the E-cad-Fc-coated dish was collected with PBS (GIBCO) containing 1 mM EDTA (ethylenediaminetetraacetic acid), and incubated (37° C.) for 1 hr under low oxygen conditions ($O_2$; 5%) and high oxygen conditions ($O_2$; 20%) in a suspension state in the same manner as with the pancreatic islet on the non-treated dish. Thereafter, the pancreatic islet was stained by incubating (37° C.) for 30 min in DMEM containing DAPI Nucleic Acid Stain (DAPI; Lonza) 5 µg/ml and Propidium iodide (PI; Roche) 0.5 µg/ml and observed under a microscope (FIG. 4).

To quantify the cell number of the pancreatic islet, the DAPI stained cell number was calculated as an index by ImageJ. Moreover, to quantify the number of the dead cells, a PI-stained cell number was calculated as an index by ImageJ. The cell death rate was calculated by the following formula:

Cell death rate (%)=(cell number stained with PI/cell number stained with DAPI)×100

Figure 4:
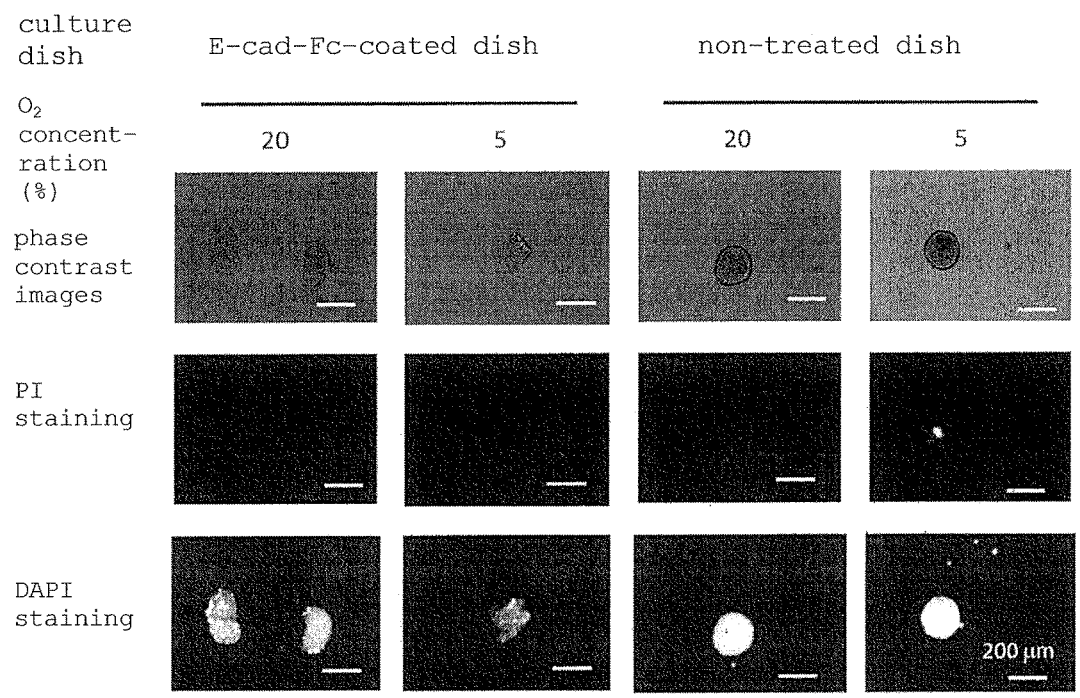
FIG. 4 shows phase contrast images of pancreatic islet at respective oxygen concentrations and the observation results of cell death by PI staining, and the total cell number by DAPI staining.
Figure 5:
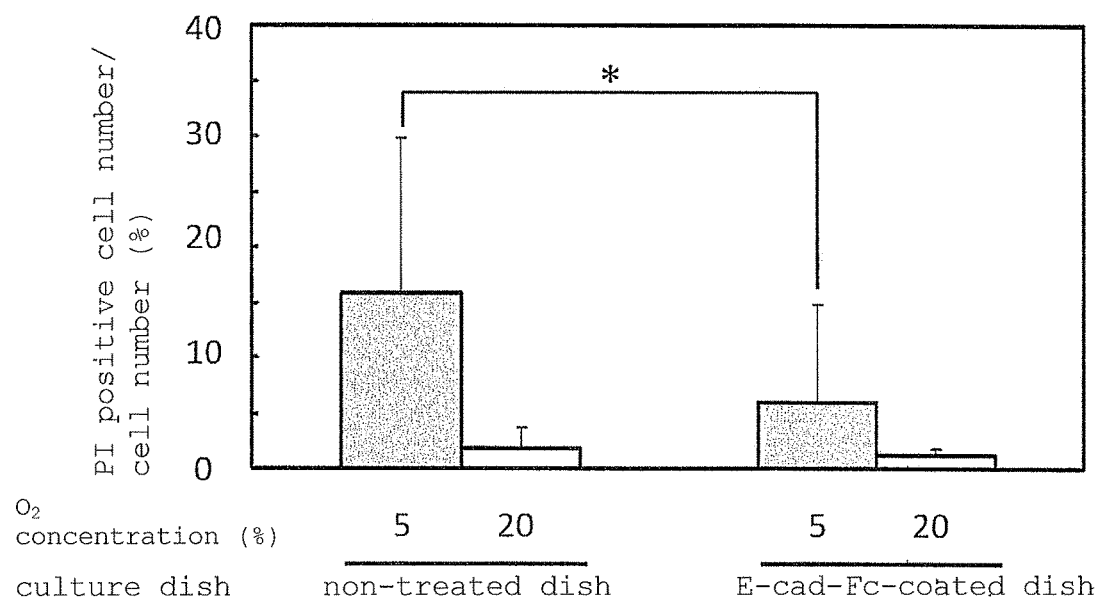
FIG. 5 shows the cell death rate of the pancreatic islet cultured on an E-cad-Fc coated dish and a non-treated dish.

The results are shown in FIGS. 4 and 5. When the oxygen concentration was 20%, the cell death induction rate was almost of the same level on the non-treated dish and E-cad-Fc-coated dish. However, when the oxygen concentration was 5%, the pancreatic islet on the non-treated dish showed positive in PI staining from the central part and the cells underwent necrosis (FIG. 4), which confirms a high cell death induction rate as compared to the pancreatic islet on the E-cad-Fc coated dish (FIG. 5). From the above, it was suggested that the cell death of the pancreatic islet cells induced under low oxygen conditions is suppressed by culturing on an E-cad-Fc-coated dish.

INDUSTRIAL APPLICABILITY

Using the method of the present invention, a sheet-like pancreatic islet having resistance to low oxygen conditions can be produced without performing a trypsin treatment while suppressing a decrease in the glucose responsive function.

In general, the pancreatic islet does not show oxygen shortage since blood vessel induction into the pancreatic islet tissue occurs in the body. However, in the case of a transplanted pancreatic islet, the cell death of the pancreatic islet may be induced by oxygen shortage under the environment of low oxygen conditions at the transplantation site. Using the sheet-like pancreatic islet obtained by the method of the present invention, oxygen can be efficiently supplied to each cell even in a low oxygen state, and the cell death of the pancreatic islet is suppressed even under low oxygen conditions, and therefore, it is advantageous for the transplantation therapy.

This application is based on a patent application No. 2011-086336 filed in Japan (filing date: Apr. 8, 2011), the contents of which are incorporated in full herein.

The invention claimed is:

1. A method of producing a sheet-like pancreatic islet, comprising: (i) preparing an isolated pancreatic islet of 200 microns or more in diameter without trypsin; (ii) plating the prepared isolated pancreatic islet of (i) onto a coated surface of a sold phase of a culture vessel, wherein the coated surface comprises a polypeptide comprising an EC1 domain of E-cadherin and having a binding ability to the E-cadherin fixed on or applied to the surface of the solid phase of the culture vessel, wherein the polypeptide is a fusion polypeptide comprising an extracellular domain of E-cadherin and an Fc region of immunoglobulin; and (iii) culturing the plated pancreatic islet of (ii) for about 6 days to 8 weeks to allow the isolated pancreatic islet to spread over the coated solid phase surface to produce a sheet of pancreatic islet, wherein the sheet of pancreatic islet shows a pancreatic islet function equal to or not less than that of a pancreatic islet cultured on a non-coated surface of the solid phase of the culture vessel.

2. The method according to claim 1, wherein the plated isolated pancreatic islet is cultured for about 10 days to 8 weeks.

* * * * *

SEQUENCE LISTING

```
<160> NUMBER OF SEQ ID NOS: 4

<210> SEQ ID NO 1
<211> LENGTH: 4815
<212> TYPE: DNA
<213> ORGANISM: Homo sapiens
<220> FEATURE:
<221> NAME/KEY: CDS
<222> LOCATION: (125)..(2773)

<400> SEQUENCE: 1
agtggcgtcg gaactgcaaa gcacctgtga gcttgcggaa gtcagttcag actccagccc        60
gctccagccc ggcccgaccc gaccgcaccc ggcgcctgcc ctcgctcggc gtccccggcc       120 agcc atg ggc cct tgg agc cgc agc ctc tcg gcg ctg ctg ctg ctg ctg       169
     Met Gly Pro Trp Ser Arg Ser Leu Ser Ala Leu Leu Leu Leu Leu
      1               5                  10                  15 cag gtc tcc tct tgg ctc tgc cag gag ccg gag ccc tgc cac cct ggc       217
Gln Val Ser Ser Trp Leu Cys Gln Glu Pro Glu Pro Cys His Pro Gly
             20                  25                  30 ttt gac gcc gag agc tac acg ttc acg gtg ccc cgg cgc cac ctg gag       265
Phe Asp Ala Glu Ser Tyr Thr Phe Thr Val Pro Arg Arg His Leu Glu
         35                  40                  45 aga ggc cgc gtc ctg ggc aga gtg aat ttt gaa gat tgc acc ggt cga       313
Arg Gly Arg Val Leu Gly Arg Val Asn Phe Glu Asp Cys Thr Gly Arg
```

|  |  |  |  |  |  |  |  |  |  |  |  |  |  |  |  |
|---|---|---|---|---|---|---|---|---|---|---|---|---|---|---|---|
|  | 50 |  |  |  | 55 |  |  |  | 60 |  |  |  |  |  |  |

```
caa  agg  aca  gcc  tat  ttt  tcc  ctc  gac  acc  cga  ttc  aaa  gtg  ggc  aca        361
Gln  Arg  Thr  Ala  Tyr  Phe  Ser  Leu  Asp  Thr  Arg  Phe  Lys  Val  Gly  Thr
 65                  70                       75 gat  ggt  gtg  att  aca  gtc  aaa  agg  cct  cta  cgg  ttt  cat  aac  cca  cag        409
Asp  Gly  Val  Ile  Thr  Val  Lys  Arg  Pro  Leu  Arg  Phe  His  Asn  Pro  Gln
 80                       85                       90                       95 atc  cat  ttc  ttg  gtc  tac  gcc  tgg  gac  tcc  acc  tac  aga  aag  ttt  tcc        457
Ile  His  Phe  Leu  Val  Tyr  Ala  Trp  Asp  Ser  Thr  Tyr  Arg  Lys  Phe  Ser
                        100                      105                      110 acc  aaa  gtc  acg  ctg  aat  aca  gtg  ggg  cac  cac  cac  cgc  ccc  ccg  ccc        505
Thr  Lys  Val  Thr  Leu  Asn  Thr  Val  Gly  His  His  His  Arg  Pro  Pro  Pro
               115                      120                      125 cat  cag  gcc  tcc  gtt  tct  gga  atc  caa  gca  gaa  ttg  ctc  aca  ttt  ccc        553
His  Gln  Ala  Ser  Val  Ser  Gly  Ile  Gln  Ala  Glu  Leu  Leu  Thr  Phe  Pro
               130                      135                      140 aac  tcc  tct  cct  ggc  ctc  aga  aga  cag  aag  aga  gac  tgg  gtt  att  cct        601
Asn  Ser  Ser  Pro  Gly  Leu  Arg  Arg  Gln  Lys  Arg  Asp  Trp  Val  Ile  Pro
          145                      150                      155 ccc  atc  agc  tgc  cca  gaa  aat  gaa  aaa  ggc  cca  ttt  cct  aaa  aac  ctg        649
Pro  Ile  Ser  Cys  Pro  Glu  Asn  Glu  Lys  Gly  Pro  Phe  Pro  Lys  Asn  Leu
160                      165                      170                      175 gtt  cag  atc  aaa  tcc  aac  aaa  gac  aaa  gaa  ggc  aag  gtt  ttc  tac  agc        697
Val  Gln  Ile  Lys  Ser  Asn  Lys  Asp  Lys  Glu  Gly  Lys  Val  Phe  Tyr  Ser
                         180                      185                      190 atc  act  ggc  caa  gga  gct  gac  aca  ccc  cct  gtt  ggt  gtc  ttt  att  att        745
Ile  Thr  Gly  Gln  Gly  Ala  Asp  Thr  Pro  Pro  Val  Gly  Val  Phe  Ile  Ile
                    195                      200                      205 gaa  aga  gaa  aca  gga  tgg  ctg  aag  gtg  aca  gag  cct  ctg  gat  aga  gaa        793
Glu  Arg  Glu  Thr  Gly  Trp  Leu  Lys  Val  Thr  Glu  Pro  Leu  Asp  Arg  Glu
               210                      215                      220 cgc  att  gcc  aca  tac  act  ctc  ttc  tct  cac  gct  gtg  tca  tcc  aac  ggg        841
Arg  Ile  Ala  Thr  Tyr  Thr  Leu  Phe  Ser  His  Ala  Val  Ser  Ser  Asn  Gly
          225                      230                      235 aat  gca  gtt  gag  gat  cca  atg  gag  att  ttg  atc  acg  gta  acc  gat  cag        889
Asn  Ala  Val  Glu  Asp  Pro  Met  Glu  Ile  Leu  Ile  Thr  Val  Thr  Asp  Gln
240                      245                      250                      255 aat  gac  aac  aag  ccc  gaa  ttc  acc  cag  gag  gtc  ttt  aag  ggg  tct  gtc        937
Asn  Asp  Asn  Lys  Pro  Glu  Phe  Thr  Gln  Glu  Val  Phe  Lys  Gly  Ser  Val
                         260                      265                      270 atg  gaa  ggt  gct  ctt  cca  gga  acc  tct  gtg  atg  gag  gtc  aca  gcc  aca        985
Met  Glu  Gly  Ala  Leu  Pro  Gly  Thr  Ser  Val  Met  Glu  Val  Thr  Ala  Thr
                    275                      280                      285 gac  gcg  gac  gat  gat  gtg  aac  acc  tac  aat  gcc  gcc  atc  gct  tac  acc       1033
Asp  Ala  Asp  Asp  Asp  Val  Asn  Thr  Tyr  Asn  Ala  Ala  Ile  Ala  Tyr  Thr
               290                      295                      300 atc  ctc  agc  caa  gat  cct  gag  ctc  cct  gac  aaa  aat  atg  ttc  acc  att       1081
Ile  Leu  Ser  Gln  Asp  Pro  Glu  Leu  Pro  Asp  Lys  Asn  Met  Phe  Thr  Ile
          305                      310                      315 aac  agg  aac  aca  gga  gtc  atc  agt  gtg  gtc  acc  act  ggg  ctg  gac  cga       1129
Asn  Arg  Asn  Thr  Gly  Val  Ile  Ser  Val  Val  Thr  Thr  Gly  Leu  Asp  Arg
320                      325                      330                      335 gag  agt  ttc  cct  acg  tat  acc  ctg  gtg  gtt  caa  gct  gct  gac  ctt  caa       1177
Glu  Ser  Phe  Pro  Thr  Tyr  Thr  Leu  Val  Val  Gln  Ala  Ala  Asp  Leu  Gln
                         340                      345                      350 ggt  gag  ggg  tta  agc  aca  aca  gca  aca  gct  gtg  atc  aca  gtc  act  gac       1225
Gly  Glu  Gly  Leu  Ser  Thr  Thr  Ala  Thr  Ala  Val  Ile  Thr  Val  Thr  Asp
                    355                      360                      365 acc  aac  gat  aat  cct  ccg  atc  ttc  aat  ccc  acc  acg  tac  aag  ggt  cag       1273
```

```
                Thr Asn Asp Asn Pro Pro Ile Phe Asn Pro Thr Thr Tyr Lys Gly Gln
                            370             375             380 gtg cct gag aac gag gct aac gtc gta atc acc aca ctg aaa gtg act            1321
Val Pro Glu Asn Glu Ala Asn Val Val Ile Thr Thr Leu Lys Val Thr
385                 390                 395 gat gct gat gcc ccc aat acc cca gcg tgg gag gct gta tac acc ata            1369
Asp Ala Asp Ala Pro Asn Thr Pro Ala Trp Glu Ala Val Tyr Thr Ile
400                 405                 410                 415 ttg aat gat gat ggt gga caa ttt gtc gtc acc aca aat cca gtg aac            1417
Leu Asn Asp Asp Gly Gly Gln Phe Val Val Thr Thr Asn Pro Val Asn
                    420                 425                 430 aac gat ggc att ttg aaa aca gca aag ggc ttg gat ttt gag gcc aag            1465
Asn Asp Gly Ile Leu Lys Thr Ala Lys Gly Leu Asp Phe Glu Ala Lys
                435                 440                 445 cag cag tac att cta cac gta gca gtg acg aat gtg gta cct ttt gag            1513
Gln Gln Tyr Ile Leu His Val Ala Val Thr Asn Val Val Pro Phe Glu
            450                 455                 460 gtc tct ctc acc acc tcc aca gcc acc gtc acc gtg gat gtg ctg gat            1561
Val Ser Leu Thr Thr Ser Thr Ala Thr Val Thr Val Asp Val Leu Asp
465                 470                 475 gtg aat gaa gcc ccc atc ttt gtg cct cct gaa aag aga gtg gaa gtg            1609
Val Asn Glu Ala Pro Ile Phe Val Pro Pro Glu Lys Arg Val Glu Val
480                 485                 490                 495 tcc gag gac ttt ggc gtg ggc cag gaa atc aca tcc tac act gcc cag            1657
Ser Glu Asp Phe Gly Val Gly Gln Glu Ile Thr Ser Tyr Thr Ala Gln
                    500                 505                 510 gag cca gac aca ttt atg gaa cag aaa ata aca tat cgg att tgg aga            1705
Glu Pro Asp Thr Phe Met Glu Gln Lys Ile Thr Tyr Arg Ile Trp Arg
                515                 520                 525 gac act gcc aac tgg ctg gag att aat ccg gac act ggt gcc att tcc            1753
Asp Thr Ala Asn Trp Leu Glu Ile Asn Pro Asp Thr Gly Ala Ile Ser
            530                 535                 540 act cgg gct gag ctg gac agg gag gat ttt gag cac gtg aag aac agc            1801
Thr Arg Ala Glu Leu Asp Arg Glu Asp Phe Glu His Val Lys Asn Ser
545                 550                 555 acg tac aca gcc cta atc ata gct aca gac aat ggt tct cca gtt gct            1849
Thr Tyr Thr Ala Leu Ile Ile Ala Thr Asp Asn Gly Ser Pro Val Ala
560                 565                 570                 575 act gga aca ggg aca ctt ctg ctg atc ctg tct gat gtg aat gac aac            1897
Thr Gly Thr Gly Thr Leu Leu Leu Ile Leu Ser Asp Val Asn Asp Asn
                    580                 585                 590 gcc ccc ata cca gaa cct cga act ata ttc ttc tgt gag agg aat cca            1945
Ala Pro Ile Pro Glu Pro Arg Thr Ile Phe Phe Cys Glu Arg Asn Pro
                595                 600                 605 aag cct cag gtc ata aac atc att gat gca gac ctt cct ccc aat aca            1993
Lys Pro Gln Val Ile Asn Ile Ile Asp Ala Asp Leu Pro Pro Asn Thr
            610                 615                 620 tct ccc ttc aca gca gaa cta aca cac ggg gcg agt gcc aac tgg acc            2041
Ser Pro Phe Thr Ala Glu Leu Thr His Gly Ala Ser Ala Asn Trp Thr
625                 630                 635 att cag tac aac gac cca acc caa gaa tct atc att ttg aag cca aag            2089
Ile Gln Tyr Asn Asp Pro Thr Gln Glu Ser Ile Ile Leu Lys Pro Lys
640                 645                 650                 655 atg gcc tta gag gtg ggt gac tac aaa atc aat ctc aag ctc atg gat            2137
Met Ala Leu Glu Val Gly Asp Tyr Lys Ile Asn Leu Lys Leu Met Asp
                    660                 665                 670 aac cag aat aaa gac caa gtg acc acc tta gag gtc agc gtg tgt gac            2185
Asn Gln Asn Lys Asp Gln Val Thr Thr Leu Glu Val Ser Val Cys Asp
                675                 680                 685
```

-continued

| | |
|---|---|
| tgt gaa ggg gcc gct ggc gtc tgt agg aag gca cag cct gtc gaa gca<br>Cys Glu Gly Ala Ala Gly Val Cys Arg Lys Ala Gln Pro Val Glu Ala<br>690 695 700 | 2233 |
| gga ttg caa att cct gcc att ctg ggg att ctt gga gga att ctt gct<br>Gly Leu Gln Ile Pro Ala Ile Leu Gly Ile Leu Gly Gly Ile Leu Ala<br>705 710 715 | 2281 |
| ttg cta att ctg att ctg ctg ctc ttg ctg ttt ctt cgg agg aga gcg<br>Leu Leu Ile Leu Ile Leu Leu Leu Leu Leu Phe Leu Arg Arg Arg Ala<br>720 725 730 735 | 2329 |
| gtg gtc aaa gag ccc tta ctg ccc cca gag gat gac acc cgg gac aac<br>Val Val Lys Glu Pro Leu Leu Pro Pro Glu Asp Asp Thr Arg Asp Asn<br>740 745 750 | 2377 |
| gtt tat tac tat gat gaa gaa gga ggc gga gaa gag gac cag gac ttt<br>Val Tyr Tyr Tyr Asp Glu Glu Gly Gly Glu Glu Asp Gln Asp Phe<br>755 760 765 | 2425 |
| gac ttg agc cag ctg cac agg ggc ctg gac gct cgg cct gaa gtg act<br>Asp Leu Ser Gln Leu His Arg Gly Leu Asp Ala Arg Pro Glu Val Thr<br>770 775 780 | 2473 |
| cgt aac gac gtt gca cca acc ctc atg agt gtc ccc cgg tat ctt ccc<br>Arg Asn Asp Val Ala Pro Thr Leu Met Ser Val Pro Arg Tyr Leu Pro<br>785 790 795 | 2521 |
| cgc cct gcc aat ccc gat gaa att gga aat ttt att gat gaa aat ctg<br>Arg Pro Ala Asn Pro Asp Glu Ile Gly Asn Phe Ile Asp Glu Asn Leu<br>800 805 810 815 | 2569 |
| aaa gcg gct gat act gac ccc aca gcc ccg cct tat gat tct ctg ctc<br>Lys Ala Ala Asp Thr Asp Pro Thr Ala Pro Pro Tyr Asp Ser Leu Leu<br>820 825 830 | 2617 |
| gtg ttt gac tat gaa gga agc ggt tcc gaa gct gct agt ctg agc tcc<br>Val Phe Asp Tyr Glu Gly Ser Gly Ser Glu Ala Ala Ser Leu Ser Ser<br>835 840 845 | 2665 |
| ctg aac tcc tca gag tca gac aaa gac cag gac tat gac tac ttg aac<br>Leu Asn Ser Ser Glu Ser Asp Lys Asp Gln Asp Tyr Asp Tyr Leu Asn<br>850 855 860 | 2713 |
| gaa tgg ggc aat cgc ttc aag aag ctg gct gac atg tac gga ggc ggc<br>Glu Trp Gly Asn Arg Phe Lys Lys Leu Ala Asp Met Tyr Gly Gly Gly<br>865 870 875 | 2761 |
| gag gac gac tag gggactcgag agaggcgggc cccagaccca tgtgctggga<br>Glu Asp Asp<br>880 | 2813 |
| aatgcagaaa tcacgttgct ggtggttttt cagctcccct cccttgagat gagtttctgg | 2873 |
| ggaaaaaaaa gagactggtt agtgatgcag ttagtatagc tttatactct ctccacttta | 2933 |
| tagctctaat aagtttgtgt tagaaaagtt tcgacttatt tcttaaagct tttttttttt | 2993 |
| tcccatcact ctttacatgg tggtgatgtc caaaagatac ccaaatttta atattccaga | 3053 |
| agaacaactt tagcatcaga aggttcaccc agcaccttgc agatttttctt aaggaatttt | 3113 |
| gtctcacttt taaaagaag gggagaagtc agctactcta gttctgttgt tttgtgtata | 3173 |
| taatttttta aaaaaaattt gtgtgcttct gctcattact acactggtgt gtccctctgc | 3233 |
| cttttttttt tttttaagac agggtctcat tctatcggcc aggctggagt gcagtggtgc | 3293 |
| aatcacagct cactgcagcc ttgtcctccc aggctcaagc tatccttgca cctcagcctc | 3353 |
| ccaagtagct gggaccacag gcatgcacca ctacgcatga ctaatttttt aaatatttga | 3413 |
| gacggggtct ccctgtgtta cccaggctgg tctcaaactc ctgggctcaa gtgatcctcc | 3473 |
| catcttggcc tcccagagta ttgggattac agacatgagc cactgcacct gcccagctcc | 3533 |
| ccaactccct gccattttt aagagacagt ttcgctccat cgcccaggcc tgggatgcag | 3593 |
| tgatgtgatc atagctcact gtaacctcaa actctggggc tcaagcagtt ctcccaccag | 3653 |

```
cctcctttt   attttttgt    acagatgggg   tcttgctatg   ttgcccaagc   tggtcttaaa    3713
ctcctggcct  caagcaatcc   ttctgccttg   gccccccaaa   gtgctgggat   tgtgggcatg    3773
agctgctgtg  cccagcctcc   atgttttaat   atcaactctc   actcctgaat   tcagttgctt    3833
tgcccaagat  aggagttctc   tgatgcagaa   attattgggc   tcttttaggg   taagaagttt    3893
gtgtctttgt  ctggccacat   cttgactagg   tattgtctac   tctgaagacc   tttaatggct    3953
tccctctttc  atctcctgag   tatgtaactt   gcaatgggca   gctatccagt   gacttgttct    4013
gagtaagtgt  gttcattaat   gtttatttag   ctctgaagca   agagtgatat   actccaggac    4073
ttagaatagt  gcctaaagtg   ctgcagccaa   agacagagcg   gaactatgaa   aagtgggctt    4133
ggagatggca  ggagagcttg   tcattgagcc   tggcaattta   gcaaactgat   gctgaggatg    4193
attgaggtgg  gtctacctca   tctctgaaaa   ttctggaagg   aatggaggag   tctcaacatg    4253
tgtttctgac  acaagatccg   tggtttgtac   tcaaagccca   gaatccccaa   gtgcctgctt    4313
ttgatgatgt  ctacagaaaa   tgctggctga   gctgaacaca   tttgcccaat   tccaggtgtg    4373
cacagaaaac  cgagaatatt   caaaattcca   aatttttttc   ttaggagcaa   gaagaaaatg    4433
tggccctaaa  gggggttagt   tgaggggtag   ggggtagtga   ggatcttgat   ttggatctct    4493
ttttatttaa  atgtgaattt   caacttttga   caatcaaaga   aaagactttt   gttgaaatag    4553
ctttactgtt  tctcaagtgt   tttggagaaa   aaaatcaacc   ctgcaatcac   tttttggaat    4613
tgtcttgatt  tttcggcagt   tcaagctata   tcgaatatag   ttctgtgtag   agaatgtcac    4673
tgtagttttg  agtgtataca   tgtgtgggtg   ctgataattg   tgtattttct   ttgggggtgg    4733
aaaaggaaaa  caattcaagc   tgagaaaagt   attctcaaag   atgcattttt   ataaatttta    4793
ttaaacaatt  ttgttaaacc   at                                                   4815
```

<210> SEQ ID NO 2
<211> LENGTH: 882
<212> TYPE: PRT
<213> ORGANISM: Homo sapiens

<400> SEQUENCE: 2

```
Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
            115                 120                 125

Gln Ala Ser Val Ser Gly Ile Gln Ala Glu Leu Leu Thr Phe Pro Asn
        130                 135                 140

Ser Ser Pro Gly Leu Arg Arg Gln Lys Arg Asp Trp Val Ile Pro Pro
145                 150                 155                 160
```

-continued

```
Ile Ser Cys Pro Glu Asn Glu Lys Gly Pro Phe Pro Lys Asn Leu Val
            165                 170                 175
Gln Ile Lys Ser Asn Lys Asp Lys Glu Gly Lys Val Phe Tyr Ser Ile
        180                 185                 190
Thr Gly Gln Gly Ala Asp Thr Pro Pro Val Gly Val Phe Ile Ile Glu
    195                 200                 205
Arg Glu Thr Gly Trp Leu Lys Val Thr Glu Pro Leu Asp Arg Glu Arg
210                 215                 220
Ile Ala Thr Tyr Thr Leu Phe Ser His Ala Val Ser Ser Asn Gly Asn
225                 230                 235                 240
Ala Val Glu Asp Pro Met Glu Ile Leu Ile Thr Val Thr Asp Gln Asn
                245                 250                 255
Asp Asn Lys Pro Glu Phe Thr Gln Glu Val Phe Lys Gly Ser Val Met
            260                 265                 270
Glu Gly Ala Leu Pro Gly Thr Ser Val Met Glu Val Thr Ala Thr Asp
        275                 280                 285
Ala Asp Asp Asp Val Asn Thr Tyr Asn Ala Ala Ile Ala Tyr Thr Ile
    290                 295                 300
Leu Ser Gln Asp Pro Glu Leu Pro Asp Lys Asn Met Phe Thr Ile Asn
305                 310                 315                 320
Arg Asn Thr Gly Val Ile Ser Val Val Thr Thr Gly Leu Asp Arg Glu
                325                 330                 335
Ser Phe Pro Thr Tyr Thr Leu Val Val Gln Ala Ala Asp Leu Gln Gly
            340                 345                 350
Glu Gly Leu Ser Thr Thr Ala Thr Ala Val Ile Thr Val Thr Asp Thr
        355                 360                 365
Asn Asp Asn Pro Pro Ile Phe Asn Pro Thr Thr Tyr Lys Gly Gln Val
    370                 375                 380
Pro Glu Asn Glu Ala Asn Val Val Ile Thr Thr Leu Lys Val Thr Asp
385                 390                 395                 400
Ala Asp Ala Pro Asn Thr Pro Ala Trp Glu Ala Val Tyr Thr Ile Leu
                405                 410                 415
Asn Asp Asp Gly Gly Gln Phe Val Val Thr Thr Asn Pro Val Asn Asn
            420                 425                 430
Asp Gly Ile Leu Lys Thr Ala Lys Gly Leu Asp Phe Glu Ala Lys Gln
        435                 440                 445
Gln Tyr Ile Leu His Val Ala Val Thr Asn Val Val Pro Phe Glu Val
    450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
                485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
        515                 520                 525
Thr Ala Asn Trp Leu Glu Ile Asn Pro Asp Thr Gly Ala Ile Ser Thr
    530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
```

```
                 580                 585                 590
Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
        755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
    850                 855                 860

Trp Gly Asn Arg Phe Lys Lys Leu Ala Asp Met Tyr Gly Gly Gly Glu
865                 870                 875                 880

Asp Asp

<210> SEQ ID NO 3
<211> LENGTH: 4413
<212> TYPE: DNA
<213> ORGANISM: Mus musculus
<220> FEATURE:
<221> NAME/KEY: CDS
<222> LOCATION: (128)..(2782)

<400> SEQUENCE: 3
actggtgtgg gagccgcggc gcactactga gttcccaaga acttctgcta gactcctgcc      60
cggcctaacc cggccctgcc cgaccgcacc cgagctcagt gtttgctcgg cgtctgccgg     120 gtccgcc atg gga gcc cgg tgc cgc agc ttt tcc gcg ctc ctg ctc ctg      169
        Met Gly Ala Arg Cys Arg Ser Phe Ser Ala Leu Leu Leu Leu
         1               5                   10 ctg cag gtc tcc tca tgg ctt tgc cag gag ctg gag cct gag tcc tgc      217
Leu Gln Val Ser Ser Trp Leu Cys Gln Glu Leu Glu Pro Glu Ser Cys
```

```
            15                  20                  25                  30
agt ccc ggc ttc agt tcc gag gtc tac acc ttc ccg gtg ccg gag agg      265
Ser Pro Gly Phe Ser Ser Glu Val Tyr Thr Phe Pro Val Pro Glu Arg
            35                  40                  45 cac ctg gag aga ggc cat gtc ctg ggc aga gtg aga ttt gaa gga tgc      313
His Leu Glu Arg Gly His Val Leu Gly Arg Val Arg Phe Glu Gly Cys
            50                  55                  60 act ggc cgg cca agg aca gcc ttc ttt tcg gaa gac tcc cga ttc aaa      361
Thr Gly Arg Pro Arg Thr Ala Phe Phe Ser Glu Asp Ser Arg Phe Lys
            65                  70                  75 gtg gcg aca gac ggc acc atc aca gtg aag cgg cat cta aag ctc cac      409
Val Ala Thr Asp Gly Thr Ile Thr Val Lys Arg His Leu Lys Leu His
 80                  85                  90 aag ctg gag acc agt ttc ctc gtc cgc gcc cgg gac tcc agt cat agg      457
Lys Leu Glu Thr Ser Phe Leu Val Arg Ala Arg Asp Ser Ser His Arg
 95                 100                 105                 110 gag ctg tct acc aaa gtg acg ctg aag tcc atg ggg cac cac cat cac      505
Glu Leu Ser Thr Lys Val Thr Leu Lys Ser Met Gly His His His His
                115                 120                 125 cgg cac cac cac cgc gac cct gcc tct gaa tcc aac cca gag ctg ctc      553
Arg His His His Arg Asp Pro Ala Ser Glu Ser Asn Pro Glu Leu Leu
            130                 135                 140 atg ttt ccc agc gtg tac cca ggt ctc aga aga cag aaa cga gac tgg      601
Met Phe Pro Ser Val Tyr Pro Gly Leu Arg Arg Gln Lys Arg Asp Trp
            145                 150                 155 gtc atc cct ccc atc agc tgc ccc gaa aat gaa aag ggc gaa ttt cca      649
Val Ile Pro Pro Ile Ser Cys Pro Glu Asn Glu Lys Gly Glu Phe Pro
            160                 165                 170 aag aac ctg gtt cag atc aaa tcc aac agg gac aaa gaa aca aag gtt      697
Lys Asn Leu Val Gln Ile Lys Ser Asn Arg Asp Lys Glu Thr Lys Val
175                 180                 185                 190 ttc tac agc atc acc ggc caa gga gct gac aaa ccc ccc gtt ggc gtt      745
Phe Tyr Ser Ile Thr Gly Gln Gly Ala Asp Lys Pro Pro Val Gly Val
                195                 200                 205 ttc atc att gag agg gag aca ggc tgg ctg aaa gtg aca cag cct ctg      793
Phe Ile Ile Glu Arg Glu Thr Gly Trp Leu Lys Val Thr Gln Pro Leu
            210                 215                 220 gat aga gaa gcc att gcc aag tac atc ctc tat tct cat gcc gtg tca      841
Asp Arg Glu Ala Ile Ala Lys Tyr Ile Leu Tyr Ser His Ala Val Ser
            225                 230                 235 tca aat ggg gaa gcg gtg gag gat ccc atg gag ata gtg atc aca gtg      889
Ser Asn Gly Glu Ala Val Glu Asp Pro Met Glu Ile Val Ile Thr Val
            240                 245                 250 aca gat cag aat gac aac agg cca gag ttt acc cag ccg gtc ttt gag      937
Thr Asp Gln Asn Asp Asn Arg Pro Glu Phe Thr Gln Pro Val Phe Glu
255                 260                 265                 270 gga ttc gtt gca gaa ggc gct gtt cca gga acc tcc gtg atg aag gtc      985
Gly Phe Val Ala Glu Gly Ala Val Pro Gly Thr Ser Val Met Lys Val
                275                 280                 285 tca gcc acc gat gca gac gat gac gtc aac acc tac aac gct gcc atc     1033
Ser Ala Thr Asp Ala Asp Asp Asp Val Asn Thr Tyr Asn Ala Ala Ile
            290                 295                 300 gcc tac acc atc gtc agc cag gat cct gag ctg cct cac aaa aac atg     1081
Ala Tyr Thr Ile Val Ser Gln Asp Pro Glu Leu Pro His Lys Asn Met
            305                 310                 315 ttc act gtc aat agg gac acc ggg gtc atc agt gtg ctc acc tct ggg     1129
Phe Thr Val Asn Arg Asp Thr Gly Val Ile Ser Val Leu Thr Ser Gly
            320                 325                 330 ctg gac cga gag agt tac cct aca tac act ctg gtg gtt cag gct gct     1177
```

```
Leu Asp Arg Glu Ser Tyr Pro Thr Tyr Thr Leu Val Val Gln Ala Ala
335                 340                 345                 350 gac ctt caa ggt gaa ggc ttg agc aca aca gcc aag gct gtg atc act      1225
Asp Leu Gln Gly Glu Gly Leu Ser Thr Thr Ala Lys Ala Val Ile Thr
                355                 360                 365 gtc aag gat att aat gac aac gct cct gtc ttc aac cca agc acg tat      1273
Val Lys Asp Ile Asn Asp Asn Ala Pro Val Phe Asn Pro Ser Thr Tyr
                370                 375                 380 cag ggt caa gtg cct gag aat gag gtc aat gcc cgg atc gcc aca ctc      1321
Gln Gly Gln Val Pro Glu Asn Glu Val Asn Ala Arg Ile Ala Thr Leu
            385                 390                 395 aaa gtg acc gat gat gat gcc ccc aac act ccg gcg tgg aaa gct gtg      1369
Lys Val Thr Asp Asp Asp Ala Pro Asn Thr Pro Ala Trp Lys Ala Val
        400                 405                 410 tac acc gta gtc aac gat cct gac cag cag ttc gtt gtt gtc aca gac      1417
Tyr Thr Val Val Asn Asp Pro Asp Gln Gln Phe Val Val Val Thr Asp
415                 420                 425                 430 ccc acg acc aat gat ggc att ttg aaa aca gcc aag ggc ttg gat ttt      1465
Pro Thr Thr Asn Asp Gly Ile Leu Lys Thr Ala Lys Gly Leu Asp Phe
                435                 440                 445 gag gcc aag cag caa tac atc ctt cat gtg aga gtg gag aac gag gaa      1513
Glu Ala Lys Gln Gln Tyr Ile Leu His Val Arg Val Glu Asn Glu Glu
            450                 455                 460 ccc ttt gag ggg tct ctt gtc cct tcc aca gcc act gtc act gtg gac      1561
Pro Phe Glu Gly Ser Leu Val Pro Ser Thr Ala Thr Val Thr Val Asp
        465                 470                 475 gtg gta gac gtg aat gaa gcc ccc atc ttt atg cct gcg gag agg aga      1609
Val Val Asp Val Asn Glu Ala Pro Ile Phe Met Pro Ala Glu Arg Arg
    480                 485                 490 gtc gaa gtg ccc gaa gac ttt ggt gtg ggt cag gaa atc aca tct tat      1657
Val Glu Val Pro Glu Asp Phe Gly Val Gly Gln Glu Ile Thr Ser Tyr
495                 500                 505                 510 acc gct cga gag ccg gac acg ttc atg gat cag aag atc acg tat cgg      1705
Thr Ala Arg Glu Pro Asp Thr Phe Met Asp Gln Lys Ile Thr Tyr Arg
                515                 520                 525 att tgg agg gac act gcc aac tgg ctg gag att aac cca gag act ggt      1753
Ile Trp Arg Asp Thr Ala Asn Trp Leu Glu Ile Asn Pro Glu Thr Gly
            530                 535                 540 gcc att ttc acg cgc gct gag atg gac aga gaa gac gct gag cat gtg      1801
Ala Ile Phe Thr Arg Ala Glu Met Asp Arg Glu Asp Ala Glu His Val
        545                 550                 555 aag aac agc aca tat gta gct ctc atc atc gcc aca gat gat ggt tca      1849
Lys Asn Ser Thr Tyr Val Ala Leu Ile Ile Ala Thr Asp Asp Gly Ser
    560                 565                 570 ccc att gcc act ggc acg ggc act ctt ctc ctg gtc ctg tta gac gtc      1897
Pro Ile Ala Thr Gly Thr Gly Thr Leu Leu Leu Val Leu Leu Asp Val
575                 580                 585                 590 aat gac aac gct ccc atc cca gaa cct cga aac atg cag ttc tgc cag      1945
Asn Asp Asn Ala Pro Ile Pro Glu Pro Arg Asn Met Gln Phe Cys Gln
                595                 600                 605 agg aac cca cag cct cat atc atc acc atc ttg gat cca gac ctt ccc      1993
Arg Asn Pro Gln Pro His Ile Ile Thr Ile Leu Asp Pro Asp Leu Pro
            610                 615                 620 ccc aac acg tcc ccc ttt act gct gag cta acc cat ggg gcc agc gtc      2041
Pro Asn Thr Ser Pro Phe Thr Ala Glu Leu Thr His Gly Ala Ser Val
        625                 630                 635 aac tgg acc att gag tat aat gac gca gct caa gaa tct ctc att ttg      2089
Asn Trp Thr Ile Glu Tyr Asn Asp Ala Ala Gln Glu Ser Leu Ile Leu
    640                 645                 650
```

-continued

| | | |
|---|---|---|
| caa cca aga aag gac tta gag att ggc gaa tac aaa atc cat ctc aag<br>Gln Pro Arg Lys Asp Leu Glu Ile Gly Glu Tyr Lys Ile His Leu Lys<br>655                          660                    665                    670 | 2137 |
| ctc gcg gat aac cag aac aaa gac cag gtg acc acg ttg gac gtc cat<br>Leu Ala Asp Asn Gln Asn Lys Asp Gln Val Thr Thr Leu Asp Val His<br>                    675                    680                    685 | 2185 |
| gtg tgt gac tgt gaa ggg acg gtc aac aac tgc atg aag gcg gga atc<br>Val Cys Asp Cys Glu Gly Thr Val Asn Asn Cys Met Lys Ala Gly Ile<br>690                          695                    700 | 2233 |
| gtg gca gca gga ttg caa gtt cct gcc atc ctc gga atc ctt gga ggg<br>Val Ala Ala Gly Leu Gln Val Pro Ala Ile Leu Gly Ile Leu Gly Gly<br>            705                    710                    715 | 2281 |
| atc ctc gcc ctg ctg att ctg atc ctg ctc cta ctg ttt cta cgg<br>Ile Leu Ala Leu Leu Ile Leu Ile Leu Leu Leu Leu Phe Leu Arg<br>720                        725                    730 | 2329 |
| agg aga acg gtg gtc aaa gag ccc ctg ctg cca cca gat gat gat acc<br>Arg Arg Thr Val Val Lys Glu Pro Leu Leu Pro Pro Asp Asp Asp Thr<br>735                          740                    745                    750 | 2377 |
| cgg gac aat gtg tat tac tat gat gaa gaa gga ggt gga gaa gaa gac<br>Arg Asp Asn Val Tyr Tyr Tyr Asp Glu Glu Gly Gly Glu Glu Asp<br>                    755                    760                    765 | 2425 |
| cag gac ttt gat ttg agc cag ctg cac agg ggc ctg gat gcc cga ccg<br>Gln Asp Phe Asp Leu Ser Gln Leu His Arg Gly Leu Asp Ala Arg Pro<br>770                        775                    780 | 2473 |
| gaa gtg act cga aat gat gtg gct ccc acc ctc atg agc gtg ccc cag<br>Glu Val Thr Arg Asn Asp Val Ala Pro Thr Leu Met Ser Val Pro Gln<br>            785                    790                    795 | 2521 |
| tat cgt ccc cgt cct gcc aat cct gat gaa att gga aac ttc atc gat<br>Tyr Arg Pro Arg Pro Ala Asn Pro Asp Glu Ile Gly Asn Phe Ile Asp<br>800                        805                    810 | 2569 |
| gaa aac ctg aag gca gcc gac agc gac ccc acg gca ccc cct tac gac<br>Glu Asn Leu Lys Ala Ala Asp Ser Asp Pro Thr Ala Pro Pro Tyr Asp<br>815                        820                    825                    830 | 2617 |
| tct ctg ttg gtg ttc gat tac gag ggc agt ggt tct gaa gcc gct agc<br>Ser Leu Leu Val Phe Asp Tyr Glu Gly Ser Gly Ser Glu Ala Ala Ser<br>                    835                    840                    845 | 2665 |
| ctg agc tca ctg aac tcc tct gag tcg gat cag gac cag gac tac gat<br>Leu Ser Ser Leu Asn Ser Ser Glu Ser Asp Gln Asp Gln Asp Tyr Asp<br>850                        855                    860 | 2713 |
| tat ctg aac gag tgg ggc aac cga ttc aag aag ctg gcg gac atg tac<br>Tyr Leu Asn Glu Trp Gly Asn Arg Phe Lys Lys Leu Ala Asp Met Tyr<br>865                        870                    875 | 2761 |
| ggc ggt ggt gag gac gac tag gggactagca agtctccccc gtgtggcacc<br>Gly Gly Gly Glu Asp Asp<br>   880 | 2812 |
| atgggagatg cagaataatt atatcagtgg tctttcagct ccttccctga gtgtgtagaa | 2872 |
| gagagactga tctgagaagt gtgcagattg catagtggtc tcactctccc tactggactg | 2932 |
| tctgtgttag gatggttttc actgattgtt gaaatctttt tttattttt atttttacag | 2992 |
| tgctgagata taaactgtgc cttttttgt ttgtttgtt ctgttttgt tcttttgagc | 3052 |
| tatgatctgc cccagacaca acagccccaa gcccctcaca cctcactaat tttttacatt | 3112 |
| gtgtacttgc cctcaattac catgtttgct gtattctaat agtcactcat gttcctgaat | 3172 |
| tctgttgccc tgcccaggtg atattctagg atgcagaaat gcctgggccc ttttatggtg | 3232 |
| agagacaggt atcttggtgt gggtgcaact gcgctggata gtgtgtgtgt tcccaagatc | 3292 |
| tttcgtggta ttccctctcc acctccagag aactcattta cagtggcatt ccttgttcgg | 3352 |
| ctatgtgtct ggggcagaac aaaaaaaagg gaccactatg catgctgcac acgtctcaga | 3412 |

-continued

```
ttcttaggta cacacctgat tcttaggtgc atgccatagt gggatatgtt gctttgatca    3472
gaacctgcag ggaggttttc gggcaccact taagtttctt ggcgtttctt tcaaaccaaa    3532
actaaagaat ggttgttctc tgagagagac tggagtgcca ccaccaaaga cagaggagag    3592
aaaaggagag aaaccaaact tggggacagc aacatcagcg aacccggcta gttggcacac    3652
cgatggtgag ggtacacagg cggtgagacc tatcccacaa gatttctgga agactaggct    3712
tatctcaacc aatgttttct ggctggaatc tttgtccatg tattcctgaa gcccaggaaa    3772
tgcacccctc caatgcctgc tcttgatggt agctacagaa aatgctggcc gatttaaacc    3832
caagttgccc agttctgagt agaaaactga gactatgctg tgtgtggcgg cgcgcacctt    3892
taagcccagc actcaggagg cagaggcagt cagatctccc tgagttcgag gccaacctgg    3952
tatatatagt atagtaagcg aattctagga cagccagggc tacacagaga aaccctgtct    4012
ctgcaaacca aaagagaaaa ctgagaatat acaaattgt gcattttctc aggaagcagg     4072
aagagaacat tctaacggga aaaaggagac aagacctttg agagttttca ttcaaaatgc    4132
aaatctcagc ttttttgataa ccactggaaa gaattttatt gaaagttctg tacttaccta   4192
actttggaag aaaatgatga ccacaatcaa ctgtgagaac tgttgatttc tctgtagttt     4252
aatcatgtaa tgttgctaga gtgacctttg tatgtagttt gagtgtatgt gtgtgggtgc   4312
tgataatttt gtattttgtg gggggtggaa aaggtaagcc attgaaaccg ttctctaaga   4372 tgcatttta tgaatttat taaagagttt tgttaaactg t                           4413
```

<210> SEQ ID NO 4
<211> LENGTH: 884
<212> TYPE: PRT
<213> ORGANISM: Mus musculus

<400> SEQUENCE: 4

```
Met Gly Ala Arg Cys Arg Ser Phe Ser Ala Leu Leu Leu Leu Gln
1               5                   10                  15

Val Ser Ser Trp Leu Cys Gln Glu Leu Glu Pro Glu Ser Cys Ser Pro
            20                  25                  30

Gly Phe Ser Ser Glu Val Tyr Thr Phe Pro Val Pro Glu Arg His Leu
        35                  40                  45

Glu Arg Gly His Val Leu Gly Arg Val Arg Phe Glu Gly Cys Thr Gly
    50                  55                  60

Arg Pro Arg Thr Ala Phe Phe Ser Glu Asp Ser Arg Phe Lys Val Ala
65                  70                  75                  80

Thr Asp Gly Thr Ile Thr Val Lys Arg His Leu Lys Leu His Lys Leu
                85                  90                  95

Glu Thr Ser Phe Leu Val Arg Ala Arg Asp Ser Ser His Arg Glu Leu
            100                 105                 110

Ser Thr Lys Val Thr Leu Lys Ser Met Gly His His His Arg His
        115                 120                 125

His His Arg Asp Pro Ala Ser Glu Ser Asn Pro Glu Leu Leu Met Phe
    130                 135                 140

Pro Ser Val Tyr Pro Gly Leu Arg Arg Gln Lys Arg Asp Trp Val Ile
145                 150                 155                 160

Pro Pro Ile Ser Cys Pro Glu Asn Glu Lys Gly Glu Phe Pro Lys Asn
                165                 170                 175

Leu Val Gln Ile Lys Ser Asn Arg Asp Lys Glu Thr Lys Val Phe Tyr
            180                 185                 190
```

```
Ser Ile Thr Gly Gln Gly Ala Asp Lys Pro Val Gly Val Phe Ile
        195             200             205
Ile Glu Arg Glu Thr Gly Trp Leu Lys Val Thr Gln Pro Leu Asp Arg
210             215             220
Glu Ala Ile Ala Lys Tyr Ile Leu Tyr Ser His Ala Val Ser Ser Asn
225             230             235             240
Gly Glu Ala Val Glu Asp Pro Met Glu Ile Val Thr Val Thr Asp
            245             250             255
Gln Asn Asp Asn Arg Pro Glu Phe Thr Gln Pro Val Phe Glu Gly Phe
            260             265             270
Val Ala Glu Gly Ala Val Pro Gly Thr Ser Val Met Lys Val Ser Ala
        275             280             285
Thr Asp Ala Asp Asp Val Asn Thr Tyr Asn Ala Ala Ile Ala Tyr
    290             295             300
Thr Ile Val Ser Gln Asp Pro Glu Leu Pro His Lys Asn Met Phe Thr
305             310             315             320
Val Asn Arg Asp Thr Gly Val Ile Ser Val Leu Thr Ser Gly Leu Asp
            325             330             335
Arg Glu Ser Tyr Pro Thr Tyr Thr Leu Val Val Gln Ala Ala Asp Leu
            340             345             350
Gln Gly Glu Gly Leu Ser Thr Thr Ala Lys Ala Val Ile Thr Val Lys
        355             360             365
Asp Ile Asn Asp Asn Ala Pro Val Phe Asn Pro Ser Thr Tyr Gln Gly
    370             375             380
Gln Val Pro Glu Asn Glu Val Asn Ala Arg Ile Ala Thr Leu Lys Val
385             390             395             400
Thr Asp Asp Asp Ala Pro Asn Thr Pro Ala Trp Lys Ala Val Tyr Thr
            405             410             415
Val Val Asn Asp Pro Asp Gln Gln Phe Val Val Thr Asp Pro Thr
            420             425             430
Thr Asn Asp Gly Ile Leu Lys Thr Ala Lys Gly Leu Asp Phe Glu Ala
        435             440             445
Lys Gln Gln Tyr Ile Leu His Val Arg Val Glu Asn Glu Glu Pro Phe
450             455             460
Glu Gly Ser Leu Val Pro Ser Thr Ala Thr Val Thr Val Asp Val Val
465             470             475             480
Asp Val Asn Glu Ala Pro Ile Phe Met Pro Ala Glu Arg Arg Val Glu
            485             490             495
Val Pro Glu Asp Phe Gly Val Gly Gln Glu Ile Thr Ser Tyr Thr Ala
            500             505             510
Arg Glu Pro Asp Thr Phe Met Asp Gln Lys Ile Thr Tyr Arg Ile Trp
        515             520             525
Arg Asp Thr Ala Asn Trp Leu Glu Ile Asn Pro Glu Thr Gly Ala Ile
    530             535             540
Phe Thr Arg Ala Glu Met Asp Arg Glu Asp Ala Glu His Val Lys Asn
545             550             555             560
Ser Thr Tyr Val Ala Leu Ile Ile Ala Thr Asp Asp Gly Ser Pro Ile
            565             570             575
Ala Thr Gly Thr Gly Thr Leu Leu Leu Val Leu Leu Asp Val Asn Asp
            580             585             590
Asn Ala Pro Ile Pro Glu Pro Arg Asn Met Gln Phe Cys Gln Arg Asn
        595             600             605
Pro Gln Pro His Ile Ile Thr Ile Leu Asp Pro Asp Leu Pro Pro Asn
```

-continued

```
            610                 615                 620
Thr Ser Pro Phe Thr Ala Glu Leu Thr His Gly Ala Ser Val Asn Trp
625                 630                 635                 640

Thr Ile Glu Tyr Asn Asp Ala Ala Gln Glu Ser Leu Ile Leu Gln Pro
                645                 650                 655

Arg Lys Asp Leu Glu Ile Gly Glu Tyr Lys Ile His Leu Lys Leu Ala
                660                 665                 670

Asp Asn Gln Asn Lys Asp Gln Val Thr Thr Leu Asp Val His Val Cys
            675                 680                 685

Asp Cys Glu Gly Thr Val Asn Asn Cys Met Lys Ala Gly Ile Val Ala
            690                 695                 700

Ala Gly Leu Gln Val Pro Ala Ile Leu Gly Ile Leu Gly Gly Ile Leu
705                 710                 715                 720

Ala Leu Leu Ile Leu Ile Leu Leu Leu Leu Phe Leu Arg Arg Arg
                725                 730                 735

Thr Val Val Lys Glu Pro Leu Leu Pro Pro Asp Asp Thr Arg Asp
                740                 745                 750

Asn Val Tyr Tyr Tyr Asp Glu Glu Gly Gly Gly Glu Glu Asp Gln Asp
                755                 760                 765

Phe Asp Leu Ser Gln Leu His Arg Gly Leu Asp Ala Arg Pro Glu Val
                770                 775                 780

Thr Arg Asn Asp Val Ala Pro Thr Leu Met Ser Val Pro Gln Tyr Arg
785                 790                 795                 800

Pro Arg Pro Ala Asn Pro Asp Glu Ile Gly Asn Phe Ile Asp Glu Asn
                805                 810                 815

Leu Lys Ala Ala Asp Ser Asp Pro Thr Ala Pro Pro Tyr Asp Ser Leu
                820                 825                 830

Leu Val Phe Asp Tyr Glu Gly Ser Gly Ser Glu Ala Ala Ser Leu Ser
                835                 840                 845

Ser Leu Asn Ser Ser Glu Ser Asp Gln Asp Gln Asp Tyr Asp Tyr Leu
                850                 855                 860

Asn Glu Trp Gly Asn Arg Phe Lys Lys Leu Ala Asp Met Tyr Gly Gly
865                 870                 875                 880

Gly Glu Asp Asp
```